US012606601B2

(12) United States Patent
Maciel Melo et al.

(10) Patent No.: US 12,606,601 B2
(45) Date of Patent: Apr. 21, 2026

(54) GENETICALLY MODIFIED MICROORGANISMS THAT CARRY OUT THE HETEROLOGOUS PRODUCTION OF MODIFIED VERSIONS OF THE SURFACTANT PROTEIN LV-RANASPUMIN-1(LV-RSN-1), THE MODIFIED VERSIONS OF SAID SURFACTANT PROTEIN, THE SYNTHETIC GENES ENCODING SAID SURFACTANT PROTEIN, THE EXPRESSION CASSETTES CONTAINING SAID SYNTHETIC GENES, AND THE EXPRESSION VECTORS CONTAINING SAID SYNTHETIC GENES

(71) Applicants: Petróleo Brasileiro S.A. - Petrobras, Rio de Janeiro (BR); Universidade Federal Do Ceará-UFC, Fortaleza (BR)

(72) Inventors: Vânia Maria Maciel Melo, Fortaleza (BR); Vinicius De Abreu Waldow, Rio de Janeiro (BR); Danuza Nogueira Moyses, Niteroi (BR); Denise Cavalcante Hissa, Fortaleza (BR); Maira Paula De Sousa, Rio de Janeiro (BR)

(73) Assignees: Petróleo Brasileiro S.A.—Petrobras, Rio de Janeiro (BR); Universidade Federal Do Ceará—UFC, Fortaleza (BR)

( * ) Notice: Subject to any disclaimer, the term of this patent is extended or adjusted under 35 U.S.C. 154(b) by 823 days.

(21) Appl. No.: 17/785,864

(22) PCT Filed: Dec. 14, 2020

(86) PCT No.: PCT/BR2020/050541
§ 371 (c)(1),
(2) Date: Jun. 15, 2022

(87) PCT Pub. No.: WO2021/119782
PCT Pub. Date: Jun. 24, 2021

(65) Prior Publication Data
US 2023/0029208 A1 Jan. 26, 2023

(30) Foreign Application Priority Data
Dec. 16, 2019 (BR) ...................... 10 2019 026867 0

(51) Int. Cl.
*C07K 14/46* (2006.01)
*B08B 9/08* (2006.01)
*C02F 3/34* (2023.01)
*C02F 101/32* (2006.01)

(52) U.S. Cl.
CPC ............. *C07K 14/463* (2013.01); *B08B 9/08* (2013.01); *C02F 3/344* (2013.01); *B08B 2209/08* (2013.01); *C02F 2101/32* (2013.01)

(58) Field of Classification Search
CPC ..... C07K 14/463; B08B 9/08; B08B 2209/08; C02F 3/344; C02F 2101/32; C02F 3/347; C12N 15/70; C12N 15/815
See application file for complete search history.

(56) References Cited

FOREIGN PATENT DOCUMENTS

| | | |
|---|---|---|
| EP | 3483248 A1 | 5/2019 |
| WO | 2019094913 A2 | 5/2019 |
| WO | 2021119782 A1 | 6/2021 |

OTHER PUBLICATIONS

Cooper et al. (Oct. 2010) "Biofoams and Natural Protein Surfactants", Biophysical Chemistry, 151(3):96-104.
Cooper et al. (2017) "Frog foams and natural protein surfactants", Colloids and surfaces. A, Physicochemical and Engineering Aspects, 534:120-129.
Hissa et al. (Mar. 2012) "Crystallization And Preliminary X-ray Diffraction Of The Surfactant Protein Lv-ranaspumin From The Frog Leptodactylus Vastus", Acta Crystallographica Section F,68(Pt 3):321-323.
Hissa et al. (Feb. 2014) "Unique Crystal Structure of a Novel Surfactant Protein from the Foam Nest of the Frog Leptodactylus vastus", ChemBioChem, 15(3):393-398.
Vance et al. (2012) "The Relationship Between Structure and Function in Natural Surfactant Proteins", University of Glasgow, 294 pages.

*Primary Examiner* — Paul J Holland
(74) *Attorney, Agent, or Firm* — Morrison & Foerster LLP

(57) ABSTRACT

The present invention refers to the heterologous production in microorganisms of modified versions of a predicted isoform of the surfactant protein Lv-ranaspumin-1 (Lv-Rsn-1), whose sequence was inferred from analyzes of the protein extract of the nest foam from the Northeastern Pepper Frog (*Leptodactylus vastus*). More specifically, it refers to two surfactant proteins that consist of modified versions of the predicted isoform of Lv-Rsn-1; to two synthetic genes each encoding one of these modified versions of the predicted isoform of Lv-Rsn-1; to two expression cassettes each containing one of the synthetic genes encoding one of the modified versions of the predicted isoform of Lv-Rsn-1; to two expression vectors each containing one of the synthetic genes encoding modified versions of the predicted isoform of Lv-Rsn-1; and to two transgenic microorganisms, a bacterium and a yeast, each transformed with one of these synthetic genes and heterologously producing one of the modified versions of the predicted isoform of Lv-Rsn-1. Lv-Rsn-1 has surfactancy, emulsification and dispersancy properties, among others, and its heterologous production allows it to be used in various applications and industrial products, without the need to extract it from the frog nest foam.

19 Claims, 11 Drawing Sheets
Specification includes a Sequence Listing.

| Before the addition of the proteins | Recombinant Lv-ranaspumin | Control with BSA |
|---|---|---|
|  |  |  |

Water        SDS        Lv-Rsn-1

GENETICALLY MODIFIED MICROORGANISMS THAT CARRY OUT THE HETEROLOGOUS PRODUCTION OF MODIFIED VERSIONS OF THE SURFACTANT PROTEIN LV-RANASPUMIN-1(LV-RSN-1), THE MODIFIED VERSIONS OF SAID SURFACTANT PROTEIN, THE SYNTHETIC GENES ENCODING SAID SURFACTANT PROTEIN, THE EXPRESSION CASSETTES CONTAINING SAID SYNTHETIC GENES, AND THE EXPRESSION VECTORS CONTAINING SAID SYNTHETIC GENES

CROSS-REFERENCE TO RELATED APPLICATIONS

This application is a national phase application, filed under 35 U.S.C. § 371, of PCT International Patent Application No. PCT/BR2020/050541, filed Dec. 14, 2020, and claims benefit of and priority to Brazilian application 10 2019 026867 0, filed on Dec. 16, 2019, the disclosures of all of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 367122003000subseqlist.txt, date recorded: Jul. 30, 2025, size: 61,175 bytes).

TECHNICAL FIELD OF THE INVENTION

The present patent application relates to the heterologous production in microorganisms of modified versions of a predicted isoform of the surfactant protein Lv-ranaspumin-1 (Lv-Rsn-1). This surfactant protein was isolated and discovered in the foam nest of the Northeastern Pepper Frog (*Leptodactylus vastus*), so that it cannot be obtained by extractivism and prevents its use in different applications. More specifically, the present patent application relates to the invention of two synthetic genes, each encoding a modified version of the predicted amino acid sequence of an Lv-Rsn-1 isoform; of two expression cassettes each containing one of these synthetic genes; of two expression vectors each containing one of these synthetic genes inserted into an expression cassette; of two genetically modified microorganisms (a bacterium and a yeast) that heterologously produce one of the modified versions of Lv-Rsn-1; and of two proteins consisting of modified versions of the Lv-Rsn-1 surfactant protein. Lv-Rsn-1 has surfactancy, emulsification and dispersancy properties, among others, and its heterologous production enables its use in various applications and products.

STATE OF THE ART

Surfactants constitute a class of amphiphilic molecules, that is: their molecular structure presents simultaneously a polar portion (hydrophilic and lipophobic) and a nonpolar portion (hydrophobic and lipophilic), and for this reason these molecules have the property of accumulating on the surfaces and interfaces of a system, reducing the free energy of those surfaces and interfaces. In this context, "surface"

usually refers to the boundary between liquid/solid or liquid/gas, while "interface" usually refers to the boundary between two immiscible liquids.

Surfactants have several applications in the agricultural, food, textile, pharmaceutical, cosmetic, domestic hygiene, oil and gas industries, among others. These applications explore the different activities of these surface-active molecules, the main ones being: emulsification, de-emulsification, solubilization and detergency (activities related to liquid-liquid interactions); the alteration of wettability and dispersancy (activities related to solid-liquid interactions); and foamability (activities related to liquid-gas interactions).

In the oil and gas industry, for example, surfactants can be used for purposes such as: (1) bioremediation of contaminated areas, when they are used to mobilize and make hydrocarbons bioavailable for biodegrading organisms; (2) cleaning up oil spills when they are used to disperse oil spills; (3) the removal of oily residues from the interior of storage tanks: (4) the control of harmful microorganisms, when they are used as biocides and antifouling agents; (5) cleaning of filtration membranes, when they are used to remove mineral deposits and biofilms that are impregnated therein; and (6) advanced oil recovery, when they are used to mobilize residual oil within reservoirs and increase the recovery factor.

The so-called chemical surfactants are those artificially synthesized from fossil precursors (petrochemicals) or plants (oleochemicals), in contrast to biosurfactants, which are those synthesized by the metabolism of living organisms. Chemical surfactants currently dominate the surfactant market, but in recent years the use of biosurfactants has been considered an increasingly attractive alternative due to properties such as: (1) greater surfactancy; (2) the lowest concentration required to reach its maximum degree of surfactancy (i.e., it has a low critical micelle concentration, or CMC); (3) lower ecotoxicity; (4) greater biodegradability; (5) increased surfactancy stability over wider pH, salinity, and temperature ranges; (6) milder production conditions, and (7) possibility of being manufactured from renewable raw materials.

The global surfactant market was estimated at US$30.6 billion in the year 2016, and is forecast to increase to US$39.8 billion by 2021, with a compound annual growth rate (CAGR) of 5.4% between 2016 and 2021. Within this universe, biosurfactants represented US$4.2 billion in 2017, and the forecast is that it will increase to US$5.5 billion by 2022, with a CAGR of 5.6% between 2017 and 2022.

Despite all the interesting properties and the numerous advantages reported in relation to chemical surfactants, the industrial production of biosurfactants still suffers from a high manufacturing cost, which is currently the biggest obstacle to a more widespread use of biosurfactants in different application areas for surfactants. This high manufacturing cost is mainly due to: (1) the high cost of raw materials. (2) the low yield of the production processes, and (3) the costs associated with the purification of biosurfactants.

The industrial production of biosurfactants can be carried out through two different approaches. The first approach is to use the species in which the biosurfactant was discovered as a production platform. This has been the hegemonic approach currently in the biosurfactant industry, which is dominated by two types of biosurfactants, both from the glycolipid class: (1) rhamnolipids (RLs) produced by bacteria of *Pseudomonas aeruginosa* species and (2) sophorolipids (SLs) produced by yeasts of the Starmerella (*Candida*) *bombicola* species. In smaller amounts, two other types of glycolipid-class biosurfactants are also commercially produced: (1) mannosyl erythritol lipids (MELs) produced by yeasts of the *Pseudozyma* gender, and (2) cellobiose lipids (CLs) produced by yeasts of the *Ustilago maydis* and *Pseudozyma flocculosa* species. Finally, there is also the commercial production of mixtures of lipopeptides (among which: fengycins, iturins, lichenisins, mycosubtilins and surfactins) or isolated surfactins, both produced by bacteria of the *Bacillus subtilis* species.

However, it is not always possible to use organisms of the same species in which the biosurfactant was discovered, and in this case the second approach that can be adopted is the genetic transformation of some microorganism so that it heterologously produces the biosurfactant of interest. The microbial strains most used industrially as platforms for heterologous production of bioproducts in general are those for which large-scale industrial cultivation and genetic transformation techniques are already well mastered, the main ones being: bacteria of the species *Bacillus subtilis, Corynebacterium* (*Micrococcus*) *glutamicum* and *Escherichia coli*, yeasts of the species *Candida albicans. Kluyveromyces lactis, Komagataella phaffii* (*Pichia pastoris*), *Saccharomyces cerevisiae* and *Yarrowia lipolytica*, and filamentous fungi of the species *Aspergillus oryzae, Aspergillus niger, Penicillium chrysogenume* and *Trichoderma reesei.*

However, the heterologous production of biosurfactants in these species presents difficulties. The most scientifically known biosurfactants that are currently produced on an industrial scale belong to the classes of glycolipids and lipopeptides, which have a nonpolar portion composed of fatty acids, and a polar portion composed respectively of carbohydrates and peptides. The biosynthesis of these biosurfactants depends on complex metabolic pathways, which involve several genes, and in order to have an idea of the complexity of this biosynthesis, the genes involved can be grouped into four main sets: (1) genes involved in the biosynthesis of the hydrophilic portion, which consists of a peptide or carbohydrate: (2) genes involved in the biosynthesis of the hydrophobic portion, which consists of a fatty acid: (3) genes involved in covalently linking the hydrophilic portion to the hydrophobic portion; and (4) genes involved in regulating the expression of genes belonging to the other three groups.

In face of that, it is possible to scale the challenge of genetic and metabolic engineering related to the heterologous production of biosurfactants of the glycolipid and lipopeptide types in the species traditionally used in biotechnological production processes. This is because the heterologous production in these species requires the insertion of a large number of genes, as well as the correct regulation of the expression of the inserted genes and the adequate supply of precursors to these metabolic pathways. These difficulties have compromised the use of the species mentioned above, so much so that the industrial production of biosurfactants is currently restricted to the species that naturally produce these biosurfactants.

In addition to the limitation of having to be produced by the microorganisms that naturally synthesize them, these biosurfactants also suffer from the additional difficulty that they are produced as mixtures of different isoforms (or congeners), and these isoforms present differences in their properties due to variations in the composition of both its hydrophobic and hydrophilic portions. Rhamnolipids, for example, may have one or two L-rhamnose-type sugars in their polar portion, and one or two β-hydroxylated fatty acids containing an even number of carbons between 8 and 16 in their nonpolar portion. The composition of the mixture of biosurfactants in terms of the proportion of each isoform is quite variable, even between batches produced with the same microbial strain and under the same culture conditions. And as there are variations in the properties of the different isoforms, the proportion of the different isoforms present in the mixture produced affects the properties of the final product, making its standardization difficult.

However, there is another class of biosurfactants, the so-called surfactant proteins, whose members have the double advantage of both circumventing the need to insert several genes and making it easier to produce a single isoform. Surfactant proteins are polymers of amino acids encoded by a single gene, which is expressed by the canonical pathway of transcribing a DNA sequence into mRNA and translating the mRNA into protein on the ribosome, according to the genetic code. In this way, it is possible to insert a single gene into a host microorganism (which facilitates the task of genetic transformation) and thus carry out the heterologous production of a single isoform (which facilitates the standardization of the final product).

Among the known natural sources of surfactant proteins, one that has been explored in recent years is the foam from frog nests, which are notable for their persistence in the environment. The first surfactant protein isolated from this source was one produced by the tùngara frog (*Physalaemus* (=*Engystomops*)*pustulosus*). Of the six proteins that were isolated from the foam of the nest from this frog (which were named ranaspumins and numbered from 1 to 6), Ep-ranaspumin-2 (Ep-Rsn-2) was the only one that showed surfactant activity, being composed by 97 amino acids and having a molecular mass of 11.0 kDa (GenBank AAP48831). Ep-Rsn-2 was able to reduce the water/air surface tension from 72 to 50 nM/m at a concentration of 10 µg/mL.

A second type of surfactant protein was isolated from the nest foam of the Northeastern Pepper Frog (*Leptodactylus vastus*) by the applicants of the present invention. This protein was isolated from the foam fluid by chromatographic techniques, and in one of the two fractions obtained, a dense and well-defined band was detected with approximately 20 kDa of molecular mass and which presented emulsifying activity (emulsification index of 57%) at 0.1 mg/mL. This protein was named Lv-ranaspumin-1 (Lv-Rsn-1).

The Lv-Rsn-1 protein isolated from the foam fluid had its amino acid sequence inferred from the crossing of information regarding the molecular mass of 23.5 kDa of its respective band in a denaturing gel electrophoresis, to sequencing by mass spectrometry of 36 peptide fragments obtained by enzymatic digestion of this band, and the electron density map obtained by X-ray crystallography, resulting in a predicted sequence of 217 amino acids. Two predicted three-dimensional structures for the crystal of this Lv-Rsn-1 protein were filed in the RCSB PDB (www.rcsb.org) under the accession codes 4K82 and 4K83.

When comparing the two isoforms of Ep-Rsn-2 and Lv-Rsn-1 whose three-dimensional structures have already been published, they present an amino acid sequence similarity of only 38%, and their three-dimensional structures are quite different: Lv-Rsn-1 has 13 bundles of α-helices and two antiparallel β-sheets constituting a clamp, while Ep-Rsn-2 is composed of four antiparallel β-sheets with an α-helix perpendicularly encircling one of its faces. Therefore, although both have been named ranaspumin because they come from frogs' nest foam, they are two clearly distinct proteins.

The results obtained when analyzing the fraction of *L. vastus* nest foam containing Lv-Rsn-1 by polyacrylamide gel electrophoresis and by sequencing of peptide fragments suggest the occurrence of other isoforms with amino acid sequences of different size and composition. However, neither the genome of *L. vastus* nor any gene that encodes any isoform of Lv-Rsn-1 has been sequenced to date, so the sequence of these other isoforms is still unknown.

Lv-Rsn-1 is a type of surfactant protein with excellent potential for different applications, and enabling its industrial production is an obstacle that needs to be overcome in order to achieve its commercialization and application for various purposes. However, considering that Lv-Rsn-1 is a biosurfactant from an animal organism, multicellular, sentient and protected by environmental legislation, the approach of using the producer organism itself is unfeasible both for technical-economic reasons and for ethical-legal issues. For similar reasons, obtaining Lv-Rsn-1 by extractivism from foams from the nest of the Northeastern Pepper Frog is also unfeasible. As far as it was possible to verify, there is no patent referring to the heterologous production of surfactant proteins from the foam of frogs' nests of any species.

In view of the disclosure, the present invention consists of two genetically modified microorganisms (a bacterium and a yeast) with the ability to produce, in a heterologous way, a modified version of the Lv-Rsn-1 surfactant protein. In addition to the two genetically modified microorganisms, the present invention also contemplates the following other inventions: (1) two proteins consisting of modified versions of a predicted isoform of the surfactant protein Lv-ranaspumin-1 (Lv-Rsn-1); (2) two synthetic genes whose sequence has been optimized for expression in bacteria and yeast, respectively, and which encode one of two modified versions of a predicted isoform of the Lv-Rsn-1 surfactant protein; (3) two bacterial and yeast expression cassettes, respectively, containing one of the synthetic genes encoding one of the modified versions of a predicted isoform of the Lv-Rsn-1 surfactant protein; and (4) two expression vectors for expression in bacteria and yeast, respectively, containing one of the synthetic genes encoding one of two modified versions of a predicted isoform of the Lv-Rsn-1 surfactant protein.

SUMMARY OF THE INVENTION

The present invention is based on the identification of the surfactant activity of the protein Lv-ranaspumin-1 (Lv-Rsn-1) produced by the Northeastern Pepper Frog (*Leptodactylus vastus*), which has potential for several industrial applications. Accordingly, the present invention contemplates two proteins that consist of modified versions of the predicted sequence of one of the isoforms of the Lv-Rsn-1 surfactant protein, neither of which occurs in nature.

Another element of the present invention refers to two synthetic genes that each encode one of the modified versions of the predicted sequence of an isoform of the Lv-Rsn-1 surfactant protein, and whose sequences were optimized for the frequency of use of codons targeting expression, respectively, in genetically modified bacterial and eukaryotic microorganisms.

Another element of the present invention refers to two expression cassettes, each containing one of the synthetic genes that encode modified versions of the predicted sequence of the Lv-Rsn-1 surfactant protein operatively linked to an active promoter, aiming at insertion into vectors of expression for replication and expression, respectively, in genetically modified bacteria and yeast.

Another element of the present invention refers to two expression vectors, each containing one of the synthetic genes that encode modified versions of the predicted sequence of an isoform of the Lv-Rsn-1 surfactant protein, targeting replication and expression, respectively, in genetically modified bacteria and yeasts.

Another element of the present invention refers to two genetically modified microorganisms, a bacterium and a yeast, each transformed with the respective expression vector containing the expression cassette with a synthetic gene that encodes the version of the predicted sequence of an isoform of the Lv-Rsn-1 surfactant protein, targeting the expression of this gene and the heterologous production of this surfactant protein.

Other objects, details and advantages of the present invention will become evident from the following figures, sequences, descriptions and examples.

BRIEF DESCRIPTION OF THE BIOLOGICAL LISTING SEQUENCE

Figure 1:
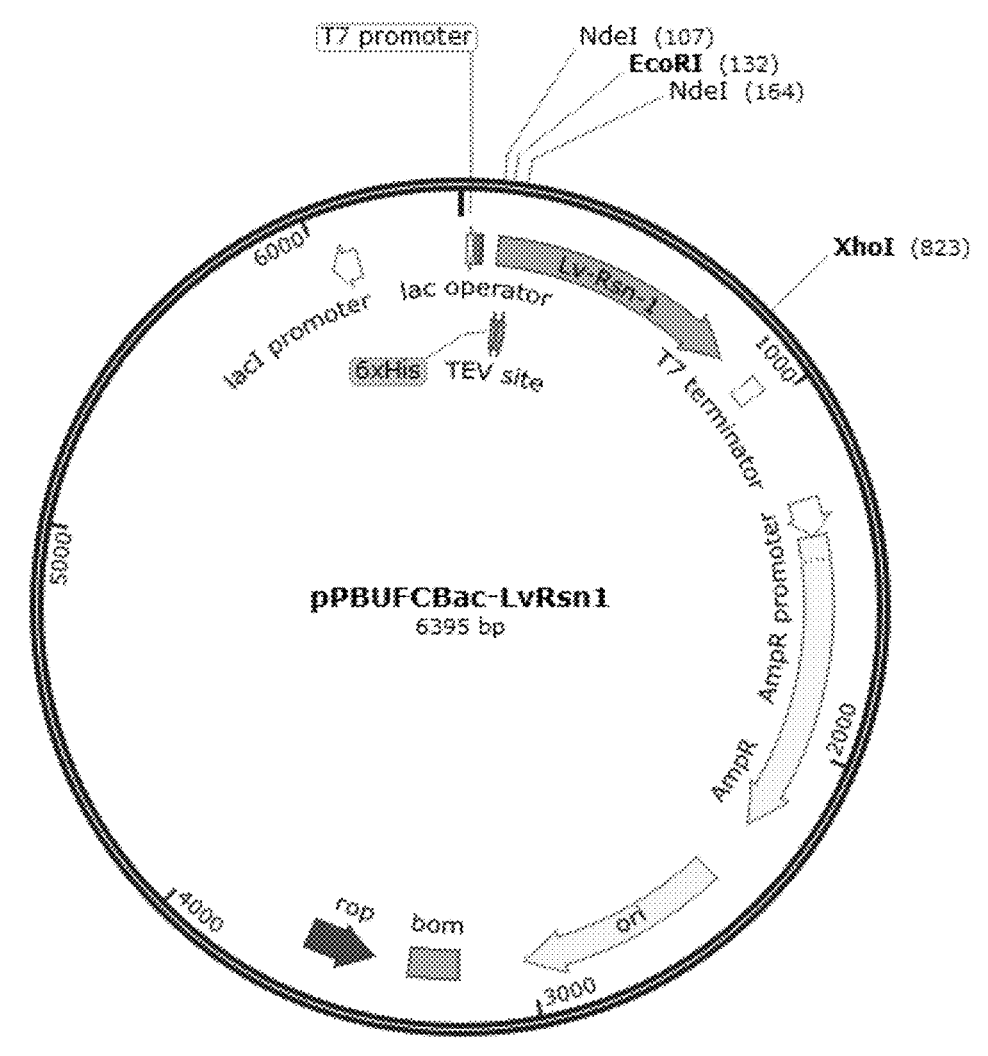
FIG. 1 shows the vector map for expression in bacteria pPBUFCBac-LvRsn1 (SEQ ID NO:8) containing the gene encoding the modified version of one of the predicted isoforms of the Lv-Rsn-1 surfactant protein (SEQ ID NO:4). On the map, the following are represented: the T7 promoter sequence (T7 promoter); the lacO operator sequence (lac operator); two restriction sites for NdeI endonuclease (NdeI) and one restriction site for endonuclease EcoRI (EcoRI); the polyhistidine tag encoding sequence (6×His); the encoding sequence for the site for cleavage by the TEV protease (TEV site); the encoding sequence of the Lv-ranaspumin-1 protein with codon frequency optimized for expression in *E. coli* (Lv-Rsn-1); the restriction site for the XhoI endonuclease; T7 terminator sequence (T7 terminator); promoter (AmpR promoter) and encoding (AmpR) sequences for a marker gene for ampicillin resistance; the origin of replication sequence of plasmid pBR322 (ori); a basis of mobility element (bom); the encoding sequence of the repressor of primer (rop) protein; and the promoter (lac promoter) and encoding (lacI) sequences for the lacI regulatory protein gene.

SEQ ID NO:1 is the predicted amino acid sequence of one of the Lv-Rsn-1 surfactant protein isoforms present in the nest foam of the Northeastern Pepper Frog (*Leptodactylus vastus*).

SEQ ID NO:2 is the nucleotide sequence resulting from the reverse translation of SEQ ID NO:1.

SEQ ID NO:4 is the nucleotide sequence resulting from SEQ ID NO:2 after having the codon usage frequency optimized for expression in bacteria, using *Escherichia coli* as a reference species.

SEQ ID NO:6 is the nucleotide sequence that contains SEQ ID NO:4 with the addition of restriction sites for endonucleases, the encoding sequence for a polyhistidine tag, and the TEV protease cleavage site encoding sequence.

SEQ ID NO:8 is the nucleotide sequence of the vector for expression in bacteria named pPBUFCBac-LvRsn1, which includes the expression cassette containing SEQ ID NO:6.

SEQ ID NO:10 is the amino acid sequence of the modified version of a predicted isoform of the Lv-Rsn-1 surfactant protein encoded by SEQ ID NO:6.

SEQ ID NO:11 is the nucleotide sequence resulting from SEQ ID NO:2 after having the codon usage frequency optimized for expression in yeast, using *Komagataella phaffii* (*Pichia pastoris*) as a reference species.

SEQ ID NO:13 is the nucleotide sequence that contains SEQ ID NO:11 with the addition of the secretion factor alpha encoding sequence, the TEV protease cleavage site encoding sequence, the Myc tag encoding sequence and the encoding sequence of a polyhistidine tag.

SEQ ID NO:15 is the nucleotide sequence of the vector for expression in yeast named pPBUFCYea-LvRsn1, which includes the expression cassette containing SEQ ID NO:11.

SEQ ID NO:17 is the amino acid sequence of the modified version of a predicted isoform of the Lv-Rsn-1 surfactant protein encoded by SEQ ID NO:13.

DESCRIPTION OF THE INVENTION

The present invention relates to the construction of two genetically modified microorganisms that heterologously produce modified versions of one of the predicted isoforms of the surfactant protein Lv-ranaspumin-1 (Lv-Rsn-1), one of which is a bacterium and the other a yeast. Additionally, the present invention relates to two modified versions of Lv-Rsn-1; to two synthetic genes that respectively encode these modified versions of Lv-Rsn-1; to two expression cassettes that respectively contain those synthetic genes that encode these modified versions of Lv-Rsn-1; and to two expression vectors each containing one of these synthetic genes encoding these modified versions of Lv-Rsn-1.

The amino acid sequence (SEQ ID NO:1) used in the present invention corresponds to the sequence of an isoform of the Lv-Rsn-1 protein predicted based on the analysis of the protein extract of the foam of the nest of *Leptodactylus vastus* by gel electrophoresis of polyacrylamide and by sequencing peptide fragments. The predicted sequence of 216 amino acids and a molecular mass of 23.3 kDa of this isoform of the Lv-Rsn-1 surfactant protein was subjected to a reverse translation using the Reverse Translation tool of the Sequence Manipulation Suite (www.bioinformatics.org/sms2/rev_trans.html) in order to obtain a nucleotide sequence that encodes its amino acid sequence (SEQ ID NO:2).

The nucleotide sequence thus obtained was then optimized, with the Codon Optimization Tool from Integrated DNA Technologies (www.idtdna.com), regarding the frequency of codon use for both expression in bacteria, using *Escherichia coli* as a reference species (SEQ ID NO:4), and for expression in yeast, using *Komagataella phaffii* (*Pichia pastoris*) as a reference species (SEQ ID NO:11).

The nucleotide sequence optimized for expression in bacteria (SEQ ID NO:4) was used to design a gene with nucleotides added downstream and upstream of SEQ ID NO:4, which consist of sites for endonucleases (which facilitate their insertion into expression vectors) and sequences encoding additional amino acid sequences (which facilitate the purification of the expressed protein).

This gene was artificially synthesized, and both this synthetic gene and a vector for expression in bacteria were digested with two endonucleases (so that the gene was inserted in the correct orientation with respect to the promoter in the expression cassette) and then joined by a DNA ligase. The expression vector thus obtained comprises an expression cassette with the synthetic gene operably linked to a promoter active in bacteria, and this expression cassette can be removed from this vector and inserted into other vectors for expression in bacteria by means of digestion with endonucleases and binding with a DNA ligase.

A strain of bacteria was genetically transformed with the expression vector containing the synthetic gene that encodes a modified version of the predicted isoform of the Lv-Rsn-1 surfactant protein. The genetically modified bacterium was cultivated in an appropriate culture medium for its reproduction and for the expression of this version of Lv-Rsn-1.

As for the yeast, the nucleotide sequence optimized for expression in yeast (SEQ ID NO:11) was used to design a gene with nucleotides added downstream and upstream of SEQ ID NO:4, which consist of sites for endonucleases (which facilitate their insertion into expression vectors) and sequences encoding additional amino acid sequences (which facilitate the purification of the expressed protein).

This gene was artificially synthesized, and both this synthetic gene and a vector for expression in yeast were digested with two endonucleases (so that the gene was inserted in the correct orientation with respect to the promoter in the expression cassette) and then joined by a DNA ligase. The expression vector thus obtained comprises an expression cassette with the synthetic gene operably linked to a promoter active in bacteria, and this expression cassette can be removed from this vector and inserted into other vectors for expression in yeast by means of digestion with endonucleases and binding with a DNA ligase.

A yeast strain was genetically transformed with the expression vector containing the synthetic gene encoding a modified version of the predicted isoform of the Lv-Rsn-1 surfactant protein. The genetically modified yeast was cultivated in an appropriate culture medium for its reproduction and for the expression of this version of Lv-Rsn-1.

EXAMPLES

The present invention may be better understood by means of the examples below. It should be noted that the present invention is not limited to the mentioned examples, and can be used in all applications described or in any other equivalent variations.

Example 1: Obtaining a Vector for the Production of Lv-Rsn-1 in Bacteria

The nucleotide sequence encoding the amino acid sequence of an isoform of the Lv-Rsn-1 surfactant protein, and which was optimized for expression in bacteria (SEQ ID NO:4) had nucleotides added, resulting in a synthetic gene (SEQ ID NO:6) which has the following composition when read in the 5' to 3' orientation: (1) the restriction site sequence for the EcoRI endonuclease with the addition of a thymine at the 3' end (5'-GAATTCT-3'); (2) the sequence (5'-GAAAACTTGTATTTCCAGGGCAGC-3') encoding the TEV protease cleavage site (ENLYFQGS); (3) the restriction site sequence for the NdeI endonuclease (5'-CATATG-3'); (4) a start codon (5'-ATG-3'); (5) the sequence encoding the amino acid sequence for a predicted isoform of the Lv-Rsn-1 surfactant protein with codon frequency optimized for expression in bacteria (SEQ ID NO:4): (6) a stop codon (5'-TAA-3'); and (7) the restriction site sequence for the XhoI endonuclease (5'-CTCGAG-3').

Figure 2:
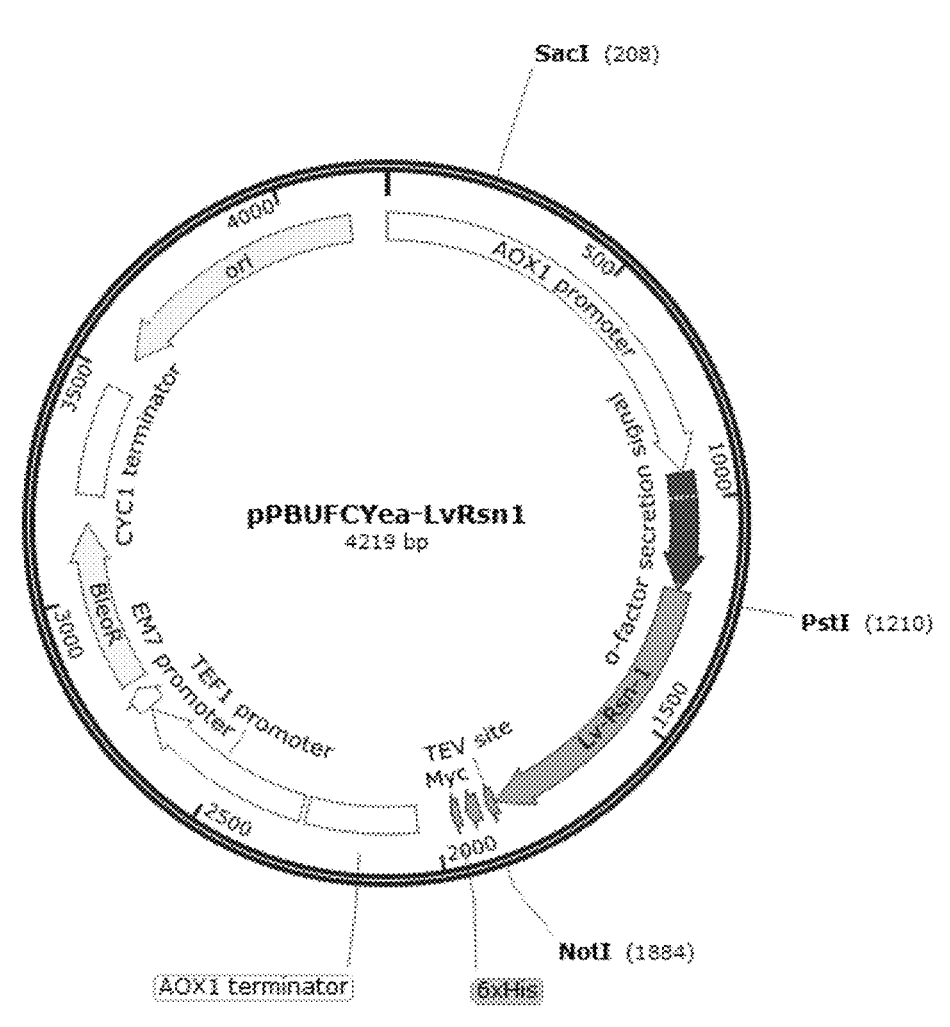
FIG. 2 shows the vector map for expression in yeast pPBUFCYea-LvRsn1 (SEQ ID NO:15) containing the gene for the modified version of one of the predicted isoforms of the Lv-Rsn-1 surfactant protein (SEQ ID NO:11). On the map, the following are represented: the AOX1 promoter sequence (AOX1 promoter): a restriction site for the endonuclease SacI (SacI); the encoding sequence of the alpha secretion factor (α-factor secretion signal); a restriction site for PstI endonuclease (PstI); the Lv-ranaspumin-1 protein encoding sequence with codon frequency optimized for expression in *K. phaffii* (Lv-Rsn-1): the encoding sequence for the site for cleavage by the TEV protease (TEV site); a restriction site for the NotI endonuclease (NotI); the c-Myc tag encoding sequence (Myc); the polyhistidine tag encoding sequence (6×His); the terminator sequence AOX1 (AOX1 terminator): the TEF1 promoter sequence (TEF1 promoter); the EM7 promoter sequence (EM7 promoter); the encoding sequence for a marker gene for zeocin resistance (BleoR); the CYC1 terminator sequence (CYC1 terminator); and the pUC plasmid origin of replication sequence (ori).

This synthetic gene (SEQ ID NO:6) and a vector for expression in bacteria were both digested with the EcoRI and XhoI endonucleases, and then joined by a DNA ligase. The final sequence of the expression vector named pPBUFCBac-LvRsn1 (SEQ ID NO:8) is shown in FIG. 2.

The modified version of a predicted isoform of the Lv-Rsn-1 surfactant protein that is encoded by the gene present in the expression vector pPBUFCYea-LvRsn1 (SEQ ID NO:8) has 236 amino acids and a molecular mass of 25.8 kDa (SEQ ID NO:10), differing from the predicted isoform by the addition of a sequence of twenty amino acids in its N-terminal portion, which contains a polyhistidine tail (HHHHHH) and a site for cleavage by the TEV protease (ENLYFQG). When this modified version of an isoform of the Lv-Rsn-1 surfactant protein is digested by the TEV protease, it differs from the predicted isoform by the presence of five amino acids (GSHMM) in its N-terminal portion.

Example 2: Obtaining Genetically Modified Bacterium

A strain of *Escherichia coli* bacterium was genetically transformed with the pPBUFCBac-LvRsn1 vector (SEQ ID NO:8) by electroporation. The strain used was one derived from the strain *E. coli* K-12, and this strain derived is: (1) auxotrophic for the leucine amino acid and sensitive to the kanamycin antibiotic; (2) it has mutations in the glutathione reductase (gor) and thioredoxin reductase (trxB) genes; and (3) it has a gene for tetracycline antibiotic resistance.

*E. coli* cells were washed 3 times with a 10% (m/v) glycerol solution to become electrocompetent, and then 1.0 µL of the solution was added with the pPBUFCBac-LvRsn1 vector (50 ηg/µL). After keeping the cell mixture with the vector for 1 min on ice, the mixture was transferred to a 0.2 cm electroporation cuvette, being subjected to a shock of 2.5 kV. After the electroporation, there were added 960 µL of SOC medium (20 g/L tryptone: 5 g/L yeast extract; 10 mM NaCl; 2.5 mM KCl; 10 mM MgCl$_2$; 10 mM MgSO$_4$; and 20 mM glucose), and the mixture was incubated at 150 rpm and 37° C. for 1 h. After the incubation time, 50 µL of the culture were inoculated into a Petri dish containing LB agar medium (10 g/L tryptone; 5 g/L yeast extract; 5 g/L NaCl; and 15 g/L of agar).

The colonies obtained were subsequently cultured in LB medium supplemented with 12.5 µg/mL of tetracycline (in order to select only cells of this strand and prevent the growth of contaminating bacteria) and 100 µg/mL of ampicillin (in order to select only transformed cells and prevent the growth of untransformed cells).

The genetic transformation with the expression vector pPBUFCBac-LvRsn1 of the colonies obtained was evaluated through the extraction of DNA from these colonies, digestion of the extracted DNA with restriction enzymes EcoRI and XhoI, and electrophoresis in agarose gel 1% (m/v) to verify the presence of the expected 692 bp fragment. The genetic transformation of *E. coli* with the expression vector pPBUFCBac-LvRsn1 was confirmed for several colonies, as well as the replication and stable inheritance of pPBUFCBac-LvRsn1 over generations.

Example 3: Production of Lv-Rsn-1 by Genetically Modified Bacteria

*E. coli* cells transformed with the pPBUFCBac-LvRsn1 vector were cultured in LB medium supplemented with isopropyl-β-D-1-thiogalactopyranoside (IPTG), a structural analogue of allolactose that interacts with the lacI protein, causing that it detaches from the lacO operator and, consequently, induces the expression of the gene encoding the modified version of an isoform of the Lv-Rsn-1 surfactant protein.

A pre-inoculum of the genetically transformed cells was obtained by transferring an isolated colony to 10 mL of LB broth supplemented with two antibiotics (12.5 µg/mL of tetracycline and 100 µg/mL of ampicillin) and then incubated at 250 rpm and 37° C. for 16 h. Then, a volume of 1 mL of the culture was transferred to flasks containing 100 mL of LB medium supplemented with 100 µg/mL of ampicillin and incubated at 37° C. and 250 rpm until reaching the exponential phase of growth (optical density at 600 nm between 0.5 and 0.7). The flasks were left to rest at room temperature for 15 min. Then, IPTG was added to a final concentration of 0.5 mM, and the culture was incubated at 200 rpm and 37° C. for 3 h. After this period, the culture was centrifuged at 7,800 g at 4° C. for 13 min, the supernatant was discarded, and the precipitate was washed with 0.1 M NaCl and centrifuged at 7,800 g at 4° C. for 1 h.

In order to purify the modified version of a predicted isoform of the Lv-Rsn-1 surfactant protein whose expression was induced by IPTG, cells were resuspended in 5 mL of resuspension buffer (50 mM Tris-HCl pH 8.0 and 150 mM NaCl) and sonicated in an ice bath for three cycles of 5 min and an amplitude of 40%. After the sonication, the cells were centrifuged at 15,000 g at 4° C. for 45 min to separate the soluble (supernatant) and insoluble (precipitate) fractions.

The purification of the modified version of the predicted isoform of the Lv-Rsn-1 surfactant protein from the insoluble fraction (precipitate containing the inclusion bodies) was performed using a resolubilization and renaturation protocol. For this, the insoluble fraction was resuspended in the washing buffer (100 mM Tris-HCl pH 8.0, 5 mM EDTA, 5 mM DTT, 2 M urea and 2% Triton X-100) and centrifuged at 22,000 g at 4° C. for 30 min. This preparation was analyzed by 15% SDS-PAGE to verify if the two washes with the buffer containing the Triton X-100 detergent and urea were sufficient to extract from the inclusion bodies most of the modified version of a predicted isoform of the Lv-Rsn-1 surfactant protein.

The purification of the modified version of a predicted isoform of the Lv-Rsn-1 surfactant protein from the supernatants of the washes with Triton X-100 and urea was performed by means of dialysis against ultrapure water followed by application in a nickel column containing silica resin previously equilibrated with 50 mM Tris-HCl pH 8.0 and 100 mM NaCl. Elution of Lv-Rsn-1 was carried out using the elution buffer corresponding to 50 mM Tris-HCl pH 8.0; 500 mM NaCl; and 250 mM imidazole.

Figure 3:
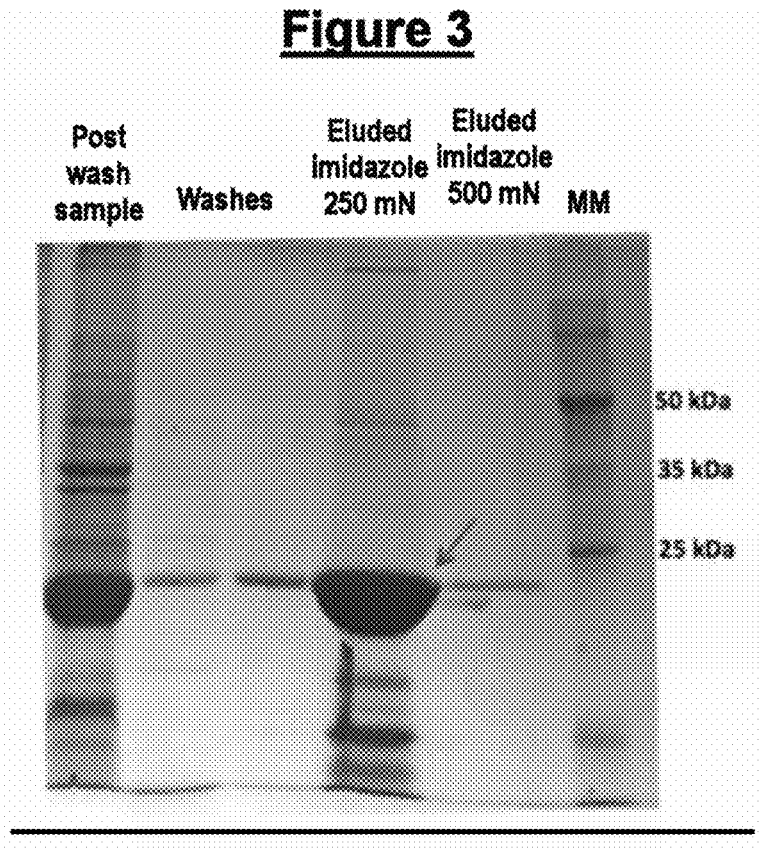
FIG. 3 shows the photo of the electrophoresis of proteins in polyacrylamide gel with sodium dodecyl sulfate (SDS-PAGE) performed to evaluate the presence of the modified version of one of the predicted isoforms of the Lv-Rsn-1 surfactant protein after the resolubilization of inclusion bodies produced by the genetically modified bacteria and purification with a nickel column. The "Post Wash" sample refers to the insoluble fraction with buffer containing Triton-X-100 detergent and Urea; the sample "Washes" refers to the washes of the unretained peak and "MM" refers to the molecular mass marker. The arrow indicates the band corresponding to the Lv-Rsn-1 surfactant protein.

Analyses by means of SDS-PAGE indicated that the modified version of a predicted isoform of the Lv-Rsn-1 surfactant protein was indeed expressed in *E. coli*. FIG. 3 shows the result of an electrophoresis of protein extracts, after the resolubilization of the inclusion bodies and the nickel column purification process (through interaction with the polyhistidine tail present in the modified version of Lv-Rsn-1). "Post Wash" refers to the insoluble fraction with buffer containing Triton-X-100 detergent and urea; "Washes" refers to washes of the unretained peak; and "MM" refers to the molecular tag. The arrow indicates the band that corresponds to Lv-Rsn-1.

The cultivation of bacteria genetically transformed with the pPBUFCBac-LvRsn1 vector (SEQ ID NO:8) demonstrated that this vector was stably inherited over several generations of cells, which began to replicate the vector and, under the presence of IPTG, to express the gene that encodes the modified version of a predicted isoform of the Lv-Rsn-1 surfactant protein, and this protein was concentrated in the inclusion bodies.

From the disclosure above, it is clear that the invention in question technically enables the heterologous production in bacteria of a modified version of a predicted isoform of the Lv-Rsn-1 surfactant protein, presenting a solution to the current state of the art, since which allows the production of this surfactant protein of animal origin without the need to collect and extract foam from the nest of the Northeastern Pepper Frog (*Leptodactylus vastus*), with all the costs and environmental impacts resulting from this collection and extraction.

Example 4: Activities of Lv-Rsn-1 Produced by Bacteria

The modified version of a predicted isoform of the Lv-Rsn-1 surfactant protein expressed in genetically transformed *E. coli* cells was purified and subjected to different assays, in order to evaluate its emulsification, water/air surface tension reduction activities, oil dispersion, and inversion of wettability.

Figure 4:
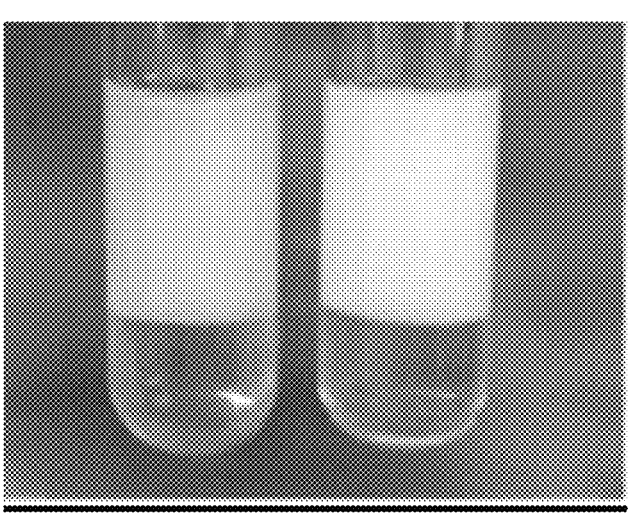
FIG. 4 shows the photo of the water/kerosene emulsification assay with 0.1 mg/mL of the modified version of one of the predicted isoforms of the Lv-Rsn-1 surfactant protein produced in *E. coli*.

The emulsifying effect on a water/kerosene mixture of the modified version of a predicted isoform of the Lv-Rsn-1 surfactant protein expressed in *E. coli* at concentrations between 0.01 to 10.0 mg/mL is shown in FIG. 4.

Figure 5:
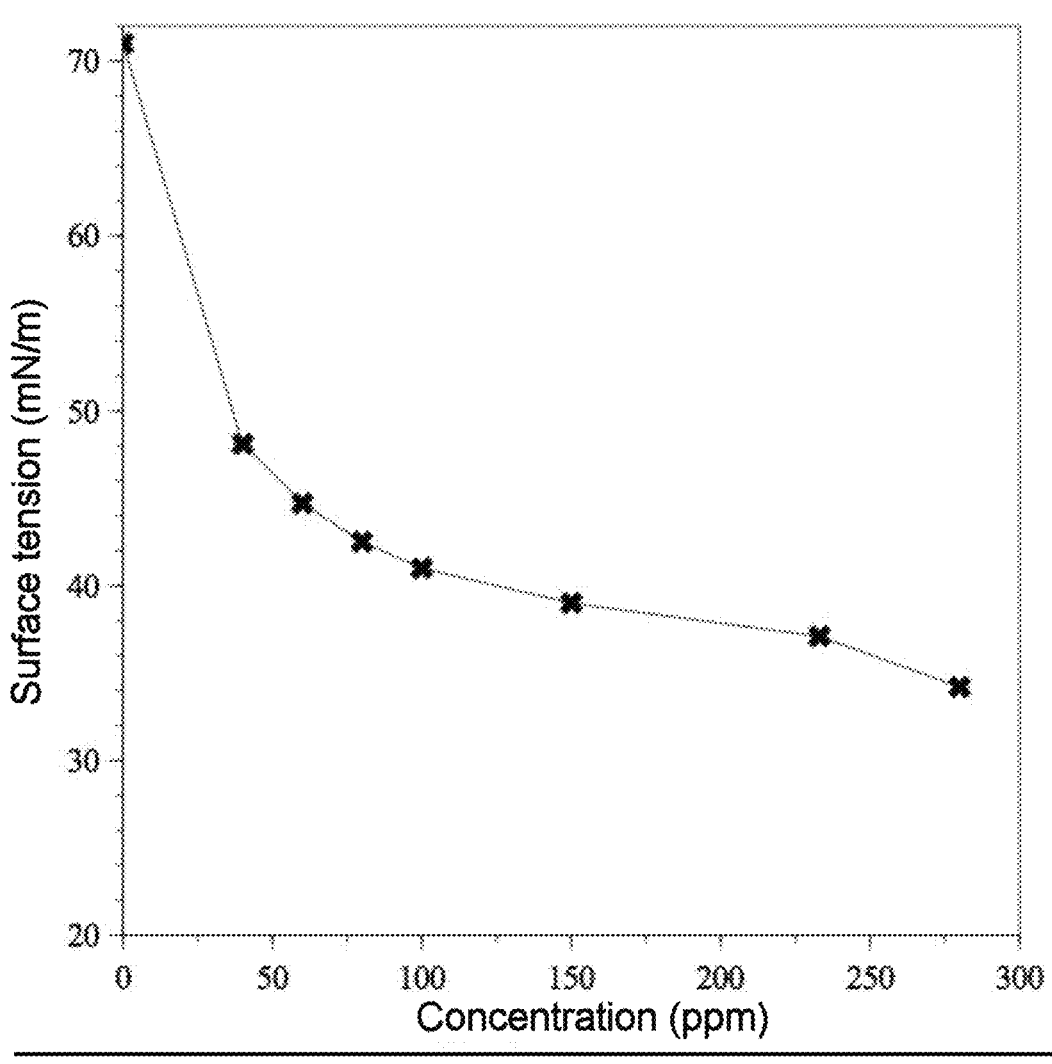
FIG. 5 shows the graph of the surfactant effect on the water/air surface tension (in mN/m) promoted by the modified version of one of the predicted isoforms of the Lv-Rsn-1 surfactant protein expressed in *E. coli* bacteria in different concentrations (in ppm).

The reduction of water/air surface tension by the modified version of a predicted isoform of the Lv-Rsn-1 surfactant protein expressed in K col. Lv-Rsn-1 at a concentration of 0.15 mg/mL reduces the surface tension of water from 72 mN/m to 39 mN/m, as shown in FIG. 5.

Figure 6:
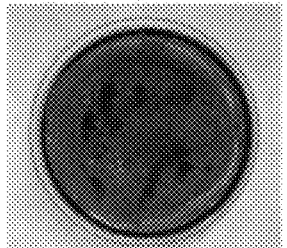
FIG. 6 shows the photos of the oil dispersion assays in seawater by 1.0 mg/L of the modified version of one of the predicted isoforms of the Lv-Rsn-1 surfactant protein expressed in bacteria (and 1.0 mg/L of bovine serum albumin protein—BSA—was used as a reference).
Figure 6:
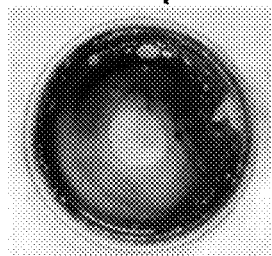
Figure 6:
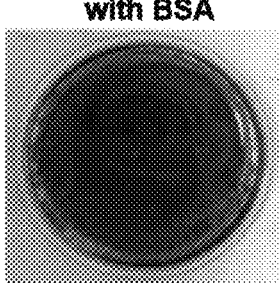

The dispersion of a layer of oil spilled in seawater by the modified version of a predicted isoform of the Lv-Rsn-1 surfactant protein expressed in *E. coli* at a concentration of 1.0 mg/L is shown in FIG. 6. The same FIG. 6 also shows the oil layer before the addition of Lv-Rsn-1 and the absence of dispersing activity of the bovine serum albumin (BSA) protein, used as a reference, also at a concentration of 1 mg/L.

Figure 7:
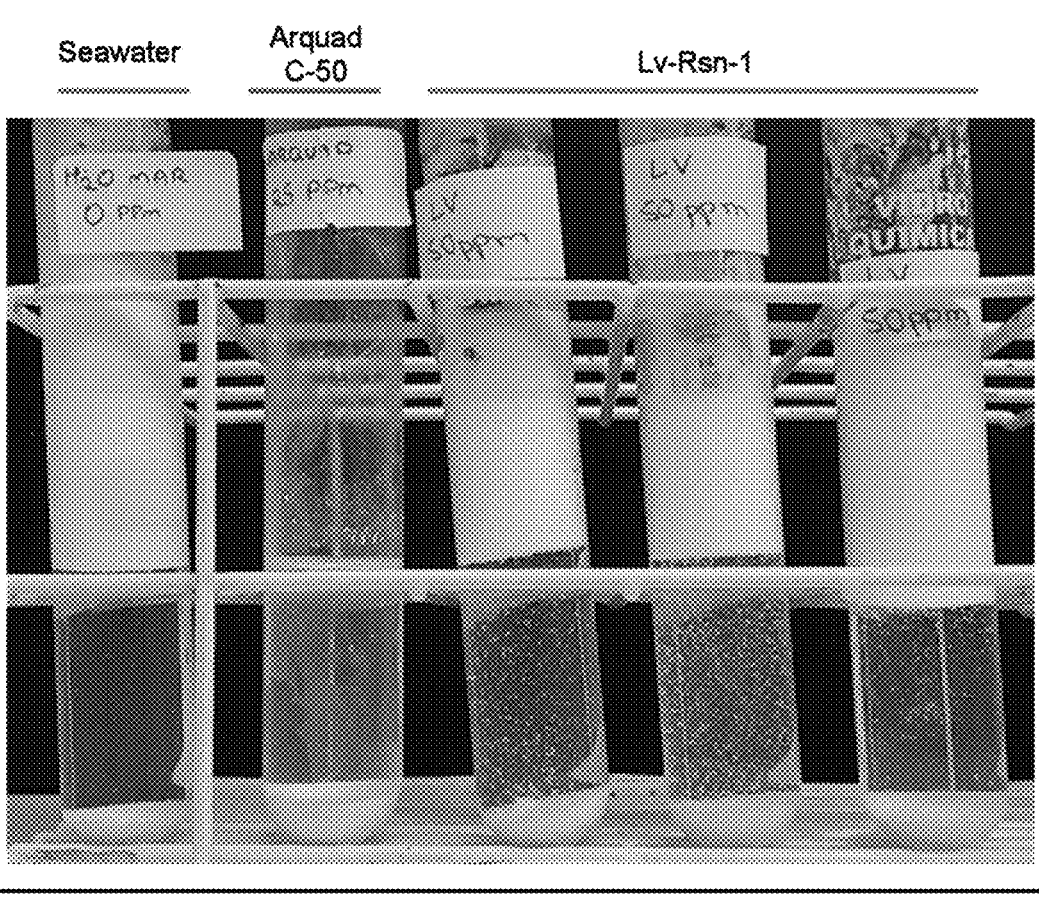
FIG. 7 shows the photo of the wettability inversion assay of calcite powder impregnated with cyclohexanepentanoic acid by 50 mg/L of the modified version of one of the predicted isoforms of the Lv-Rsn-1 surfactant protein expressed in bacteria. Seawater was used as a negative control, and 25 mg/L of Arquad C-50 cationic surfactant was used as a positive control.

The inversion of the wettability of a calcite powder (CaCO$_3$) impregnated with cyclohexanepentanoic acid by the modified version of a predicted isoform of the Lv-Rsn-1 surfactant protein expressed in *E. coli* at a concentration of 50 mg/L is shown in FIG. 7. The inversion of wettability is measured by the presence of a greater amount of calcite powder at the bottom of the test tube compared to the negative control (seawater).

From the disclosure above, it is clear that the modified version of a predicted isoform of the Lv-Rsn-1 surfactant protein expressed in *E. coli* acts as a surfactant, emulsifier, dispersant and wettability inverter, and can be applied to different purposes associated with these activities.

Example 5: Obtaining a Vector for the Production of Lv-Rsn-1 in Yeast

The nucleotide sequence optimized for expression in yeast (SEQ ID NO:11) had nucleotides added, resulting in a synthetic gene (SEQ ID NO:13) that has the following composition when read in the 5' to 3' orientation: (1) the restriction site for PstI endonuclease (5'-CTGCAG-3'); (2) two nucleotides (5'-GN-3') to place the Lv-Rsn-1 encoding sequence in the same translation frame as the alpha secretion factor; (3) the sequence encoding the Lv-Rsn-1 surfactant protein with codon frequency optimized for yeast expression (SEQ ID NO:11); (4) the sequence (5'-GAGAACCTT-TACTTTCAGGGA-3') encoding the TEV protease cleavage site (ENLYFQG); and (5) the restriction site for the NotI endonuclease (5'-GCGGCCCC-3').

This synthetic gene (SEQ ID NO:13) and a vector for expression in yeast were both digested with the PstI and NotI endonucleases, and then joined by a DNA ligase. The final sequence of the expression vector named pPBUFCYea-LvRsn1 (SEQ ID NO:15) is shown in FIG. 3.

The modified version of a predicted isoform of the Lv-Rsn-1 surfactant protein that is encoded by the gene present in the expression vector pPBUFCYea-LvRsn1 (SEQ ID NO:15) has 341 amino acids and a molecular mass of 36.7 kDa (SEQ ID NO:17), differing from the isoform predicted by the addition of the secretion factor alpha plus two amino acids in its N-terminal portion, and the site for cleavage by the TEV protease, plus six amino acids, the c-Myc tag, plus five amino acids and a polyhistidine tail in the C-terminal portion. When this modified version of a predicted isoform of the Lv-Rsn-1 surfactant protein is digested by the TEV protease, it differs from the predicted isoform by the presence of 91 amino acids in its N-terminal portion and 6 amino acids in its C-terminal portion.

Example 6: Obtaining a Genetically Modified Yeast

A yeast strain of the species *Komagataella phaffii* was genetically transformed with the vector pPBUFCYea-LvRsn1 (SEQ ID NO:15) by electroporation. The strain used is the strain *Komagataella phaffii* GS 115/ATCC 20864, and this strain is auxotrophic for the histidine amino acid (HIS4⁻) and has active genes for AOX1 and AOX2 (Mut⁺), so that they can use methanol as a nutrient.

*K. phaffii* cells were prepared by inoculating an isolated colony in 5.0 mL of YPD medium (10 g/L of yeast extract; 20 g/L of peptone; and 20 g/L of glucose) and incubating them at 30° C. for 16 h at 250 rpm. Then, 250 μL of the cultures were transferred to 500 mL of YPD broth in a 2.0 L container and incubated at 250 rpm at 30° C. for approximately 16 h, until obtaining an optical density at 600 nm between 1.3 and 1.6. Then, the cultures were centrifuged at 1,500 g for 5 min at 4° C. The supernatants were discarded, and the precipitates containing the cells were gently resuspended in 500 ml of ice-cold ultrapure water. Then, the cells were centrifuged again and the precipitates resuspended in 250 ml of ice-cold ultrapure water. The cells were centrifuged, and the pellets were resuspended in 20 ml of ice-cold 1.0 M D-sorbitol. Finally, the cells were centrifuged and resuspended in 1.0 ml of ice-cold 1.0 M D-sorbitol, thus resulting in electrocompetent cells that were used for genetic transformation.

In preparation for genetic transformation, the vector pPBUFCYea-LvRsn1 (SEQ ID NO:15) was linearized with the SacI endonuclease, and the linearized vector was then purified using a potassium acetate precipitation protocol. To this end, 3.0 M potassium acetate pH 5.5 was added to a final concentration of 0.3 M, followed by the addition of 2 volumes of 100% ethanol and incubation at −20° C. for 30 min. Then, the mixture was centrifuged at 12,000 g for 10 min at 4° C., the precipitate was washed with 70% ethanol and centrifuged again. After drying the plasmid at 37° C. for 10 min, it was resuspended in ultrapure water, quantified by spectrophotometry, and stored in a freezer at −20° C.

For genetic transformation, a 90 μL volume of the solution containing electrocompetent *K. phaffii* cells was mixed with 5 to 10 μg of pPBUFCYea-LvRsn1 vector DNA (SEQ ID NO:15) linearized in a 600 μL microtube, and the final volume was transferred to a 0.2 cm electroporation cuvette previously cooled on ice. The cuvette containing the cells and the linearized vector was incubated on ice for 5 min and then subjected to a pulse of 2.5 kV in an electroporator. Immediately, 1.0 mL of ice-cold 1.0 M D-sorbitol was added to the cuvette, and the contents were then transferred to a 15 mL tube. The tube was incubated at 30° C. for 2 h without agitation. Then, a volume of 200 μL of the tube contents was inoculated onto a plate containing YDPS Agar medium (10 g/L yeast extract; 20 g/L peptone, 20 g/L glucose; 182.2 g/L of D-sorbitol and 15 g/L of agar) supplemented with 100 μg/mL of the zeocin antibiotic. The plates were incubated at 30° C. in the oven for 3 to 10 days, until colonies appeared. The transformed clones were cultured in YPD medium and stored at −80° C. after supplementation with 20% (v/v) glycerol. The transformed clones were sequentially subjected to increasing concentrations of zeocin (500, 1000 and 2000 μg/mL) in YPD Agar medium, in order to select transformants containing multiple copies of the pPBUFC-Yea-LvRsn1 vector (SEQ ID NO:15).

In order to confirm the success of the genetic transformation, genomic DNA from colonies of cells resistant to 2,000 μg/mL zeocin was extracted using the cetyl trimethylammonium bromide (CTAB) protocol. At the end of the extraction, the DNA obtained was eluted in 50 pd of 10 mM Tris-HCl pH 8.0 supplemented with 20 μg/μL of RNAse. Samples were quantified and evaluated by absorbance measurements at 230, 260 and 280 nm in a spectrophotometer and later stored in a freezer at −20° C. The detection of the presence of the gene that encodes the modified version of the Lv-Rsn-1 surfactant protein in the transformed clones was performed using the polymerase chain reaction (PCR) technique using the primers AOX1-fwd (5'-GACTGGTTC-CAATTGACAAGC-3') and AOX1-rev (5'-GCAAATGG-CATTCTGACATCC-3'). PCR reactions were performed in a final volume of 25 μL, containing 50 ng of genomic DNA; 20 mM Tris-HCl (pH 8.4); 3.0 mM MgCl₂; 0.2 mM of each dNTP; 0.5 μM of each primer; and 1.0 unit of Taq DNA polymerase. The reactions were performed in a thermocycler programmed for an initial denaturation step (5 min at 94° C.), followed by 30 cycles of 1 min at 94° C., 1 min at 52° C. and 1.5 min at 72° C. The last cycle was followed by a final extension of 10 min at 72° C. PCR products were visualized in 1.0% (m/v) agarose gel electrophoresis, stained with SYBR Green and having a 1 kb marker as a reference. The genetic transformation of *K. phaffii* with the expression vector pPBUFCYea-LvRsn1 (SEQ ID NO:15) was confirmed, as well as the stable inheritance of this transformation Across Generations.

Example 7: Confirmation of Lv-Rsn-1 Production by Yeast

*K. phaffii* cells transformed with pPBUFCYea-LvRsn1 vector (SEQ ID NO:15) were cultured at 30° C. on plates containing YPD Agar medium (10 g/L yeast extract; 20 g/L of peptone; 20 g/L of glucose; and 15 g/L of agar) supplemented with 100 μg/mL of the antibiotic zeocin. For the pre-inoculum, pure colonies were cultured in 200 mL of BMGH medium (13.4 g/L of yeast extract with ammonium sulfate and without amino acids; 10 mL/L of glycerol; 100 mL/L of phosphate buffer 1.0 M pH 6.0; 2.0 mL/L of 0.02% biotin: 10 mL/L of 0.4% histidine; and 100 µg/mL of zeocin) at 29° C. for 16 h at 250 rpm until achieve an optical density at 600 nm of approximately 2.0. Then, the culture was centrifuged at 3,500 rpm for 5 min, and the precipitate was washed twice with BMMH medium (13.4 g/L of yeast extract with ammonium sulfate and without amino acids; 100 mL/L of buffer 1.0 M phosphate pH 6.0; 2.0 mL/L of 0.02% biotin; 10 mL/L of 0.4% histidine; and 0.5% v/v methanol) to remove the glycerol present in the BMGH medium used in the pre-inoculum.

After this step, the cells were resuspended and inoculated into a 500 mL flask containing 50 mL of BMMH with an optical density at 600 nm of 1.0. The cultures were incubated under agitation at 250 rpm at 29° C. for 96 h, with the optical density at 6(0) nm monitored every 24 h, when the culture was supplemented with 0.5% (v/v) methanol. At the end of 96 h, the culture was centrifuged at 3,000 g for 5 min.

The expression of the modified version of the predicted isoform of the Lv-Rsn-1 surfactant protein by *K. phaffii* was monitored by Tricine-SDS-PAGE. Before being applied to electrophoresis gels, the samples from the supernatants were precipitated with acetone and the samples from the precipitate (0.3 mg) were mixed with 0.3 mL of sample buffer (2 mL of SDS; 1.2 mL of glycerol; 0.2 mL of β-mercaptoethanol; 1.0 mg of Coomassie Brilliant Blue G-250; and 0.5 mL of Tris-HCl pH 6.8 for a final volume of 10 mL) and incubated at 100° C. for 10 min. The results obtained indicated that the modified version of a predicted isoform of the Lv-Rsn-1 surfactant protein was expressed by *K. phaffii*, and this characteristic was maintained over the generations.

Subsequently, the same *K. phaffii* cells transformed with the pPBUFCYea-LvRsn1 vector were cultured in bioreactors with a volume of 5.0 L. For the pre-inoculum, pure colonies were cultured in six 2.0 L flasks containing 200 mL of BMGH medium supplemented with 100 µg/mL ampicillin at 29° C. and 250 rpm for 16 h until reaching an optical density at 600 nm of approximately 2.0. These cultures were pooled, the final volume was centrifuged at 3,000 rpm for 5 min, and the precipitate washed twice with BMMH expression medium to remove the remaining glycerol. Subsequently, the cells were resuspended in 100 ml of BMMH medium and this volume was transferred to the bioreactor resulting in an optical density at 600 nm of approximately 1.5.

Figure 8:
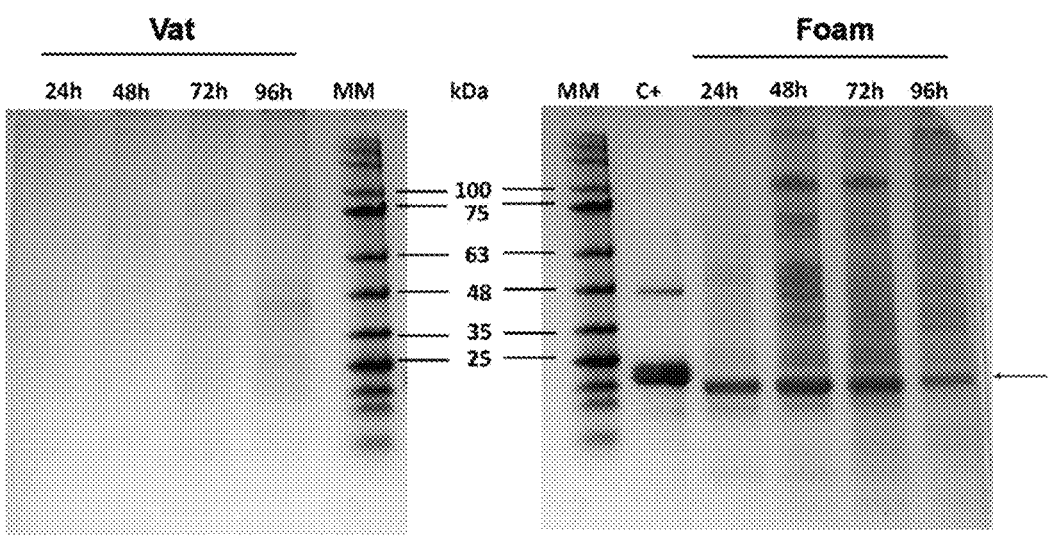
FIG. 8 shows the photo of tricine sodium dodecyl sulfate polyacrylamide gel electrophoresis (Tricine-SDS-PAGE) to evaluate the presence of the modified version of one of the predicted isoforms of the Lv-Rsn-1 surfactant protein in the vat supernatant and in the foam of the cultivation of genetically modified *K. phaffii* in a 5-liter bioreactor after 24, 48, 72 and 96 hours of the addition of 0.5% (v/v) of methanol. MM=molecular marker; C+=version of the Lv-Rsn-1 protein produced by *E. coli*; and the red arrow points to the band corresponding to the modified version of one of the Lv-Rsn-1 protein isoforms produced by *K. phaffii*.

The cultures were carried out in batches with a maximum volume of 3.0 L of BMMH expression medium supplemented with 100 µg/mL of zeocin at 29° C., 500 rpm and aeration of 1 vvm. Optical density at initial 600 nm was recorded, and the culture received 0.5% (v/v) methanol. This procedure was repeated every 24 h until 96 h. Every 24 h, the volume of foam that overflowed in the Mariotte flask was collected, which was connected to the bioreactor to collect the foam that overflowed from the vat. This liquefied foam was centrifuged at 9,000 rpm for 10 min at 4° C. The foam protein concentration was quantified, and the protein profile analyzed by Tricine-SDS-PAGE 15%. The results obtained indicated that the modified version of Lv-Rsn-1 produced by *K. phaffii* in 5.0 L bioreactors was concentrated in the foam, as can be seen in FIG. 8.

Example 8: Activities of Lv-Rsn-1 Produced by Yeast

The modified version of the predicted isoform of the Lv-Rsn-1 surfactant protein expressed in genetically transformed *K. phaffii* cells cultured in the 5.0 L bioreactor was purified and subjected to different assays in order to evaluate its emulsification activities, reduction of water/air surface tension, and inversion of wettability.

Figure 9:
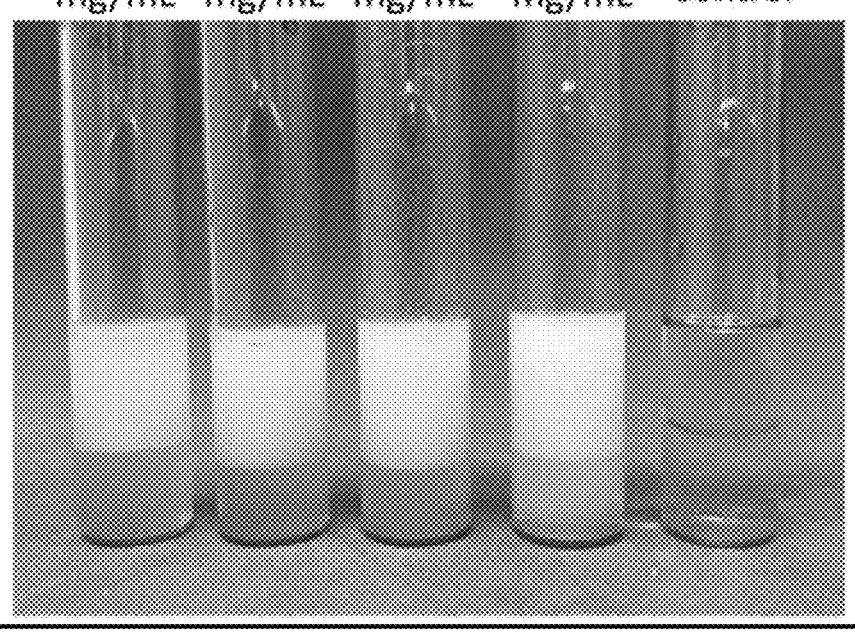
FIG. 9 shows the photo of the water/kerosene emulsification assay with different concentrations of the modified version of one of the predicted isoforms of the Lv-Rsn-1 surfactant protein produced in *K. phaffii*; the negative control consists of BMMH medium at pH 6.0.

The emulsifying effect on a water/kerosene mixture of the modified version of a predicted isoform of the Lv-Rsn-1 surfactant protein in *K. phaffii* at concentrations between 0.03 to 0.24 mg/mL is shown in FIG. 9.

Figure 10:
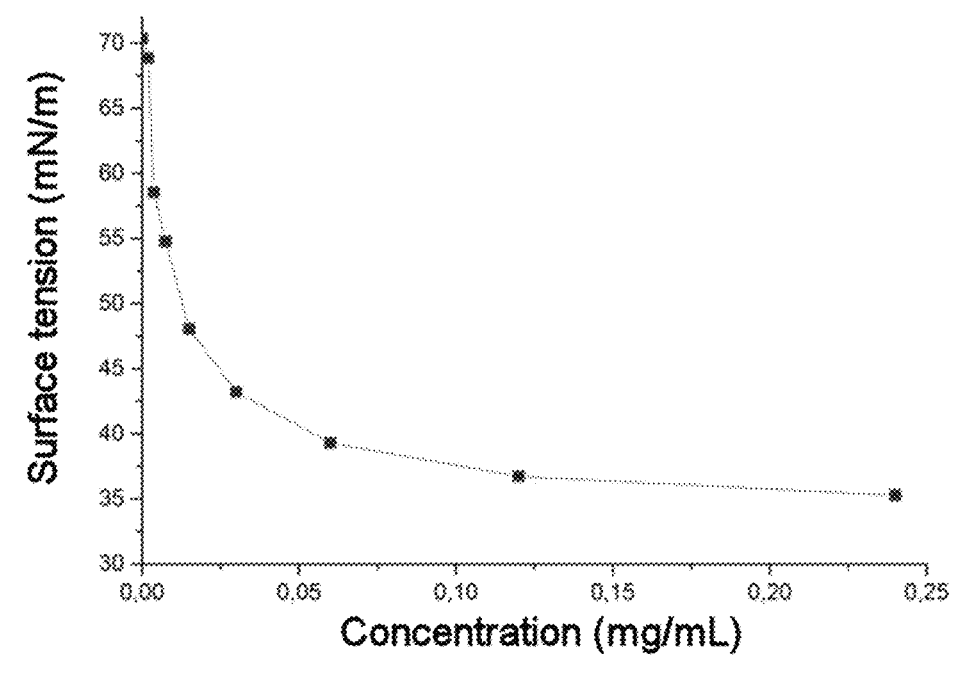
FIG. 10 shows the graph of the surfactant effect on the water/air surface tension (in mN/m) promoted by the modified version of one of the predicted isoforms of the Lv-Rsn-1 surfactant protein expressed in the *K. phaffii* yeast in different concentrations (in mg/mL).

The reduction of water/air surface tension by the modified version of a predicted isoform of the Lv-Rsn-1 surfactant protein expressed in *K. phaffii*. Lv-Rsn-1 at a concentration of 0.24 mg/mL reduces the surface tension of water from 72 mN/m to 35 mN/m, as shown in FIG. 10.

Figure 11:
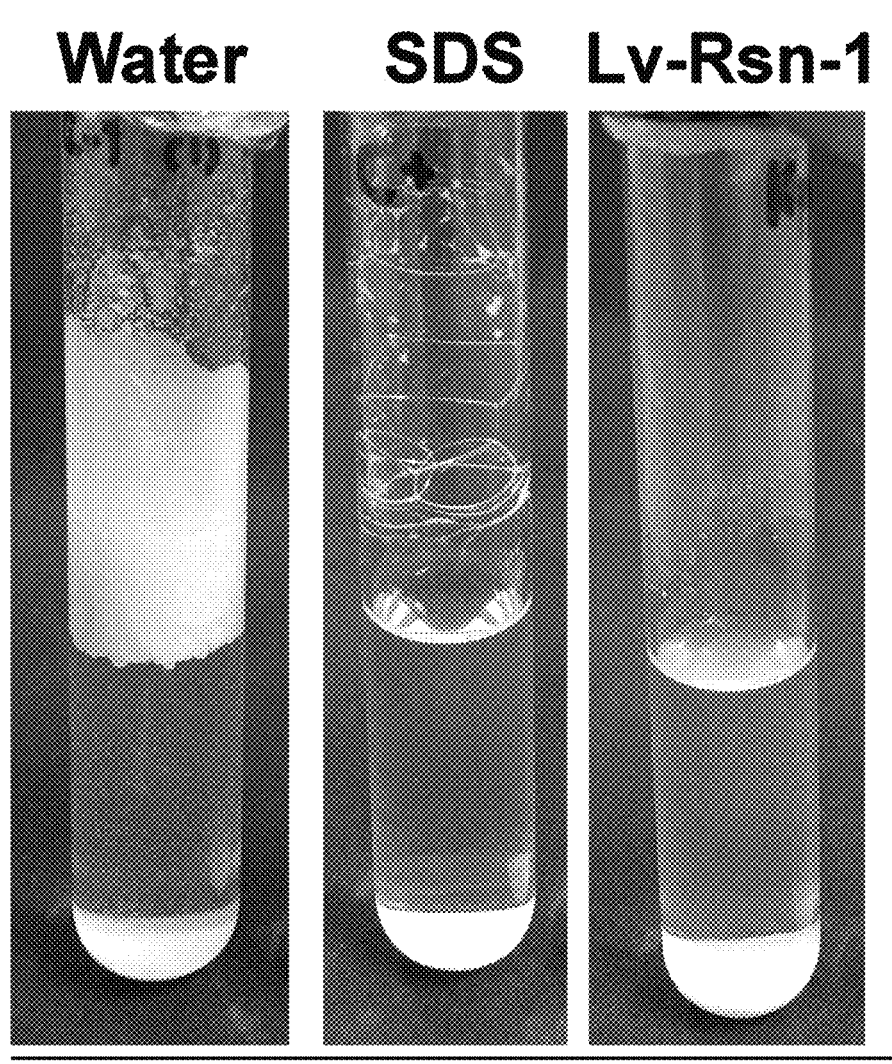
FIG. 11 shows the photo of the inversion wettability assay of calcite powder impregnated with cyclohexanepentanoic acid by 50 mg/L of the modified version of one of the predicted isoforms of the Lv-Rsn-1 surfactant protein expressed in bacteria. Seawater was used as a negative control, and 25 mg/L of the anionic surfactant sodium dodecyl sulfate (SDS) was used as a positive control.

The inversion of wettability of a calcite powder ($CaCO_3$) impregnated with cyclohexanepentanoic acid by the modified version of a predicted isoform of the Lv-Rsn-1 surfactant protein expressed in *K. phaffii* at a concentration of 50 mg/L is shown in FIG. 11. The inversion of wettability is measured by the presence of a greater amount of calcite powder at the bottom of the test tube compared to the negative control (seawater). As a positive control, sodium dodecyl sulfate (SDS) was used at a concentration of 2,500 mg/L.

From the disclosure above, it is clear that the modified version of a predicted isoform of the Lv-Rsn-1 surfactant protein expressed in *K. phaffii* acts as a surfactant, emulsifier, dispersant and wettability inverter, and can be applied to different purposes associated with these activities.

Those skilled in the subject will appreciate that numerous variations focusing on the scope of protection of the application are allowed and, thus, it reinforces the fact that the present invention is not limited to the particular configurations and embodiments described above.

---

The invention claimed is:

1. A polynucleotide comprising the nucleotide sequence of SEQ ID NO: 2, wherein the polynucleotide encodes an isoform of the surfactant protein Lv-ranaspumin-1 (Lv-Rsn-1).

2. A polynucleotide comprising the nucleotide sequence of SEQ ID NO: 4, wherein the polynucleotide encodes an isoform of the surfactant protein Lv-ranaspumin-1 (Lv-Rsn-1) comprising a codon frequency optimized for expression in bacteria.

3. A polynucleotide comprising the nucleotide sequence of SEQ ID NO: 11, wherein the polynucleotide encodes an isoform of the surfactant protein Lv-ranaspumin-1 (Lv-Rsn-1) comprising a codon frequency optimized for expression in yeast.

4. A polypeptide comprising the amino acid sequence of SEQ ID NO: 10, wherein the polypeptide is a modified version of an isoform of the surfactant protein Lv-ranaspumin-1 (Lv-Rsn-1).

5. A polypeptide comprising the amino acid sequence of SEQ ID NO: 17, wherein the polypeptide is a modified version of an isoform of the surfactant protein Lv-ranaspumin-1 (Lv-Rsn-1).

6. An expression cassette comprising the polynucleotide according to claim 2 operably linked to a promoter that directs expression in bacteria.

7. An expression cassette comprising the polynucleotide according to claim 3 operably linked to a promoter that directs expression in fungi.

8. An expression vector comprising the expression cassette according to claim 6.

9. An expression and transformation vector comprising the expression cassette according to claim 7.

10. A genetically modified micro-organism, wherein the micro-organism is a bacterium that produces a protein encoded by the polynucleotide according to claim 6.

11. A genetically modified micro-organism, wherein the micro-organism is a yeast that produces a protein encoded by the polynucleotide according to claim 7.

12. A process of production of a genetically modified micro-organism comprising:
   a) transforming one or more bacterial cells with the expression cassette according to claim 6;
   b) selecting one or more bacterial cells transformed with said expression cassette.

13. A process of production of a genetically modified micro-organism comprising:
   a) transforming one or more yeast cells with the expression cassette according to claim 7;
   b) selecting one or more yeast cells transformed with said expression cassette.

14. A product comprising the polypeptide according to claim 4.

15. A product comprising the polypeptide according to claim 5.

16. An advanced oil recovery process comprising mobilizing residual oil within a reservoir with a biosurfactant protein encoded by the polynucleotide according to claim 1, wherein the biosurfactant protein is synthesized by a genetically modified organism capable of synthesizing the biosurfactant protein Lv-ranaspumin-1.

17. An oil bioremediation process comprising mobilizing and making hydrocarbons bioavailable for biodegrading organisms with a biosurfactant protein encoded by the polynucleotide according to claim 1, wherein the biosurfactant protein is synthesized by a genetically modified organism capable of synthesizing the biosurfactant protein Lv-ranaspumin-1.

18. A tank cleaning process in the oil and gas industry comprising removal of oily residues from the interior of storage tanks with a biosurfactant protein encoded by the polynucleotide according to claim 1, wherein the biosurfactant protein is synthesized by a genetically modified organism capable of synthesizing the biosurfactant protein Lv-ranaspumin-1.

19. The expression cassette of claim 7, wherein the fungi comprises yeast.

* * * * *

SEQUENCE LISTING

<160> NUMBER OF SEQ ID NOS: 17

<210> SEQ ID NO 1
<211> LENGTH: 216
<212> TYPE: PRT
<213> ORGANISM: Leptodactylus vastus
<220> FEATURE:
<221> NAME/KEY: MISC_FEATURE
<223> OTHER INFORMATION: Predicted sequence for one of the isoforms of
      LV-Ranaspumin-1

<400> SEQUENCE: 1

Leu Leu Glu Gly Phe Leu Val Gly Gly Gly Val Pro Gly Pro Gly Thr
1               5                   10                  15

```
Ala Cys Leu Thr Lys Ala Leu Lys Asp Ser Gly Asp Leu Leu Val Glu
            20                  25                  30

Leu Ala Val Ile Ile Cys Ala Tyr Gln Asn Gly Lys Asp Leu Gln Glu
            35                  40                  45

Gln Asp Phe Lys Glu Leu Lys Glu Leu Leu Glu Arg Thr Leu Glu Arg
        50                  55                  60

Ala Gly Cys Ala Leu Asp Asp Ile Val Ala Asp Leu Gly Leu Glu Glu
65                  70                  75                  80

Leu Leu Gly Ser Ile Gly Val Ser Thr Gly Asp Ile Ile Gln Gly Leu
                85                  90                  95

Tyr Lys Leu Leu Lys Glu Leu Lys Ile Asp Glu Thr Val Phe Asn Ala
            100                 105                 110

Val Cys Asp Val Thr Lys Lys Met Leu Asp Asn Lys Cys Leu Pro Lys
            115                 120                 125

Ile Leu Gln Gly Asp Leu Val Lys Phe Leu Asp Leu Lys Tyr Lys Val
        130                 135                 140

Cys Ile Glu Gly Gly Asp Pro Glu Leu Ile Ile Lys Asp Leu Lys Ile
145                 150                 155                 160

Ile Leu Glu Arg Leu Pro Cys Val Leu Gly Gly Val Gly Leu Asp Asp
                165                 170                 175

Leu Phe Lys Asn Ile Phe Val Lys Asp Gly Ile Leu Ser Phe Glu Gly
            180                 185                 190

Ile Ala Lys Pro Leu Gly Asp Leu Leu Ile Leu Val Leu Cys Pro Asn
            195                 200                 205

Val Lys Asn Ile Asn Val Ser Ser
        210                 215

<210> SEQ ID NO 2
<211> LENGTH: 648
<212> TYPE: DNA
<213> ORGANISM: Artificial sequence
<220> FEATURE:
<223> OTHER INFORMATION: Synthetic construct
<220> FEATURE:
<221> NAME/KEY: CDS
<222> LOCATION: (1)..(648)
<220> FEATURE:
<221> NAME/KEY: misc_feature
<222> LOCATION: (1)..(648)
<223> OTHER INFORMATION: Coding sequence of one of the Lv-ranaspumin-1
      isoforms after reverse translation of the predicted amino acid
      sequence

<400> SEQUENCE: 2 ctg ctg gaa ggc ttt ctg gtg ggc ggc ggc gtg ccg ggc ccg ggc acc        48
Leu Leu Glu Gly Phe Leu Val Gly Gly Gly Val Pro Gly Pro Gly Thr
1               5                   10                  15 gcg tgc ctg acc aaa gcg ctg aaa gat agc ggc gat ctg ctg gtg gaa        96
Ala Cys Leu Thr Lys Ala Leu Lys Asp Ser Gly Asp Leu Leu Val Glu
            20                  25                  30 ctg gcg gtg att att tgc gcg tat cag aac ggc aaa gat ctg cag gaa       144
Leu Ala Val Ile Ile Cys Ala Tyr Gln Asn Gly Lys Asp Leu Gln Glu
            35                  40                  45 cag gat ttt aaa gaa ctg aaa gaa ctg ctg gaa cgc acc ctg gaa cgc       192
Gln Asp Phe Lys Glu Leu Lys Glu Leu Leu Glu Arg Thr Leu Glu Arg
        50                  55                  60 gcg ggc tgc gcg ctg gat gat att gtg gcg gat ctg ggc ctg gaa gaa       240
Ala Gly Cys Ala Leu Asp Asp Ile Val Ala Asp Leu Gly Leu Glu Glu
65                  70                  75                  80
```

```
ctg ctg ggc agc att ggc gtg agc acc ggc gat att att cag ggc ctg          288
Leu Leu Gly Ser Ile Gly Val Ser Thr Gly Asp Ile Ile Gln Gly Leu
             85                  90                  95 tat aaa ctg ctg aaa gaa ctg aaa att gat gaa acc gtg ttt aac gcg          336
Tyr Lys Leu Leu Lys Glu Leu Lys Ile Asp Glu Thr Val Phe Asn Ala
            100                 105                 110 gtg tgc gat gtg acc aaa aaa atg ctg gat aac aaa tgc ctg ccg aaa          384
Val Cys Asp Val Thr Lys Lys Met Leu Asp Asn Lys Cys Leu Pro Lys
            115                 120                 125 att ctg cag ggc gat ctg gtg aaa ttt ctg gat ctg aaa tat aaa gtg          432
Ile Leu Gln Gly Asp Leu Val Lys Phe Leu Asp Leu Lys Tyr Lys Val
            130                 135                 140 tgc att gaa ggc ggc gat ccg gaa ctg att att aaa gat ctg aaa att          480
Cys Ile Glu Gly Gly Asp Pro Glu Leu Ile Ile Lys Asp Leu Lys Ile
145                 150                 155                 160 att ctg gaa cgc ctg ccg tgc gtg ctg ggc ggc gtg ggc ctg gat gat          528
Ile Leu Glu Arg Leu Pro Cys Val Leu Gly Gly Val Gly Leu Asp Asp
                165                 170                 175 ctg ttt aaa aac att ttt gtg aaa gat ggc att ctg agc ttt gaa ggc          576
Leu Phe Lys Asn Ile Phe Val Lys Asp Gly Ile Leu Ser Phe Glu Gly
            180                 185                 190 att gcg aaa ccg ctg ggc gat ctg ctg att ctg gtg ctg tgc ccg aac          624
Ile Ala Lys Pro Leu Gly Asp Leu Leu Ile Leu Val Leu Cys Pro Asn
            195                 200                 205 gtg aaa aac att aac gtg agc agc                                          648
Val Lys Asn Ile Asn Val Ser Ser
            210                 215

<210> SEQ ID NO 3
<211> LENGTH: 216
<212> TYPE: PRT
<213> ORGANISM: Artificial sequence
<220> FEATURE:
<223> OTHER INFORMATION: Synthetic Construct

<400> SEQUENCE: 3

Leu Leu Glu Gly Phe Leu Val Gly Gly Gly Val Pro Gly Pro Gly Thr
1               5                   10                  15

Ala Cys Leu Thr Lys Ala Leu Lys Asp Ser Gly Asp Leu Leu Val Glu
            20                  25                  30

Leu Ala Val Ile Ile Cys Ala Tyr Gln Asn Gly Lys Asp Leu Gln Glu
            35                  40                  45

Gln Asp Phe Lys Glu Leu Lys Glu Leu Leu Glu Arg Thr Leu Glu Arg
        50                  55                  60

Ala Gly Cys Ala Leu Asp Asp Ile Val Ala Asp Leu Gly Leu Glu Glu
65                  70                  75                  80

Leu Leu Gly Ser Ile Gly Val Ser Thr Gly Asp Ile Ile Gln Gly Leu
            85                  90                  95

Tyr Lys Leu Leu Lys Glu Leu Lys Ile Asp Glu Thr Val Phe Asn Ala
            100                 105                 110

Val Cys Asp Val Thr Lys Lys Met Leu Asp Asn Lys Cys Leu Pro Lys
            115                 120                 125

Ile Leu Gln Gly Asp Leu Val Lys Phe Leu Asp Leu Lys Tyr Lys Val
            130                 135                 140

Cys Ile Glu Gly Gly Asp Pro Glu Leu Ile Ile Lys Asp Leu Lys Ile
145                 150                 155                 160

Ile Leu Glu Arg Leu Pro Cys Val Leu Gly Gly Val Gly Leu Asp Asp
                165                 170                 175
```

```
Leu Phe Lys Asn Ile Phe Val Lys Asp Gly Ile Leu Ser Phe Glu Gly
            180                 185                 190

Ile Ala Lys Pro Leu Gly Asp Leu Leu Ile Leu Val Leu Cys Pro Asn
        195                 200                 205

Val Lys Asn Ile Asn Val Ser Ser
    210                 215

<210> SEQ ID NO 4
<211> LENGTH: 651
<212> TYPE: DNA
<213> ORGANISM: Artificial sequence
<220> FEATURE:
<223> OTHER INFORMATION: Synthetic construct
<220> FEATURE:
<221> NAME/KEY: CDS
<222> LOCATION: (1)..(651)
<220> FEATURE:
<221> NAME/KEY: misc_feature
<222> LOCATION: (1)..(651)
<223> OTHER INFORMATION: Codon frequency optimization of SEQ ID NO:2 for
      expression in bacteria and addition of the ATG start codon

<400> SEQUENCE: 4 atg ctg ctg gaa ggt ttt ctg gtt ggg ggc ggt gtt ccg ggt cca ggc      48
Met Leu Leu Glu Gly Phe Leu Val Gly Gly Gly Val Pro Gly Pro Gly
1               5                   10                  15 acg gcc tgc ttg acg aag gct ctg aaa gat agc ggt gac ctg ctg gtg      96
Thr Ala Cys Leu Thr Lys Ala Leu Lys Asp Ser Gly Asp Leu Leu Val
            20                  25                  30 gag tta gcg gtt att att tgt gca tac cag aat ggc aaa gac ctt cag     144
Glu Leu Ala Val Ile Ile Cys Ala Tyr Gln Asn Gly Lys Asp Leu Gln
        35                  40                  45 gag cag gac ttc aaa gaa ctg aag gaa ttg ctg gaa cgt aca ttg gaa     192
Glu Gln Asp Phe Lys Glu Leu Lys Glu Leu Leu Glu Arg Thr Leu Glu
    50                  55                  60 cgt gcc ggt tgt gcc ctc gat gat att gtg gcc gat tta ggt ctg gaa     240
Arg Ala Gly Cys Ala Leu Asp Asp Ile Val Ala Asp Leu Gly Leu Glu
65                  70                  75                  80 gaa ctg ctg ggc tcc atc ggc gtt agt acc ggc gat att atc cag ggt     288
Glu Leu Leu Gly Ser Ile Gly Val Ser Thr Gly Asp Ile Ile Gln Gly
                85                  90                  95 ctg tat aaa ctg ttg aag gag tta aaa atc gac gag acc gtc ttt aat     336
Leu Tyr Lys Leu Leu Lys Glu Leu Lys Ile Asp Glu Thr Val Phe Asn
            100                 105                 110 gcg gtc tgc gat gtg acc aaa aaa atg ctg gat aac aag tgc tta ccg     384
Ala Val Cys Asp Val Thr Lys Lys Met Leu Asp Asn Lys Cys Leu Pro
            115                 120                 125 aaa att ctg caa gga gat ctg gta aag ttc ctt gat ctg aag tat aaa     432
Lys Ile Leu Gln Gly Asp Leu Val Lys Phe Leu Asp Leu Lys Tyr Lys
        130                 135                 140 gtt tgt att gaa ggt ggc gat cca gaa ctg att att aag gat ctg aaa     480
Val Cys Ile Glu Gly Gly Asp Pro Glu Leu Ile Ile Lys Asp Leu Lys
145                 150                 155                 160 atc atc ctg gaa cgg ctt ccg tgt gtg ttg ggt gga gtc ggt ttg gat     528
Ile Ile Leu Glu Arg Leu Pro Cys Val Leu Gly Gly Val Gly Leu Asp
                165                 170                 175 gat ctc ttt aag aac att ttt gtt aag gat ggg att ctg tcc ttc gaa     576
Asp Leu Phe Lys Asn Ile Phe Val Lys Asp Gly Ile Leu Ser Phe Glu
            180                 185                 190 ggt att gcg aaa cct ctt ggt gac ctt ctc atc ctt gtc tta tgc ccg     624
Gly Ile Ala Lys Pro Leu Gly Asp Leu Leu Ile Leu Val Leu Cys Pro
            195                 200                 205
```

-continued

```
aac gtc aag aat atc aat gta tcc tct                                  651
Asn Val Lys Asn Ile Asn Val Ser Ser
    210                 215
```

```
<210> SEQ ID NO 5
<211> LENGTH: 217
<212> TYPE: PRT
<213> ORGANISM: Artificial sequence
<220> FEATURE:
<223> OTHER INFORMATION: Synthetic Construct

<400> SEQUENCE: 5

Met Leu Leu Glu Gly Phe Leu Val Gly Gly Gly Val Pro Gly Pro Gly
1               5                   10                  15

Thr Ala Cys Leu Thr Lys Ala Leu Lys Asp Ser Gly Asp Leu Leu Val
            20                  25                  30

Glu Leu Ala Val Ile Ile Cys Ala Tyr Gln Asn Gly Lys Asp Leu Gln
        35                  40                  45

Glu Gln Asp Phe Lys Glu Leu Lys Glu Leu Leu Glu Arg Thr Leu Glu
    50                  55                  60

Arg Ala Gly Cys Ala Leu Asp Asp Ile Val Ala Asp Leu Gly Leu Glu
65                  70                  75                  80

Glu Leu Leu Gly Ser Ile Gly Val Ser Thr Gly Asp Ile Ile Gln Gly
                85                  90                  95

Leu Tyr Lys Leu Leu Lys Glu Leu Lys Ile Asp Glu Thr Val Phe Asn
            100                 105                 110

Ala Val Cys Asp Val Thr Lys Lys Met Leu Asp Asn Lys Cys Leu Pro
            115                 120                 125

Lys Ile Leu Gln Gly Asp Leu Val Lys Phe Leu Asp Leu Lys Tyr Lys
    130                 135                 140

Val Cys Ile Glu Gly Gly Asp Pro Glu Leu Ile Ile Lys Asp Leu Lys
145                 150                 155                 160

Ile Ile Leu Glu Arg Leu Pro Cys Val Leu Gly Gly Val Gly Leu Asp
                165                 170                 175

Asp Leu Phe Lys Asn Ile Phe Val Lys Asp Gly Ile Leu Ser Phe Glu
                180                 185                 190

Gly Ile Ala Lys Pro Leu Gly Asp Leu Leu Ile Leu Val Leu Cys Pro
            195                 200                 205

Asn Val Lys Asn Ile Asn Val Ser Ser
    210                 215
```

```
<210> SEQ ID NO 6
<211> LENGTH: 697
<212> TYPE: DNA
<213> ORGANISM: Artificial sequence
<220> FEATURE:
<223> OTHER INFORMATION: Synthetic construct
<220> FEATURE:
<221> NAME/KEY: CDS
<222> LOCATION: (2)..(688)
<220> FEATURE:
<221> NAME/KEY: misc_feature
<222> LOCATION: (2)..(688)
<223> OTHER INFORMATION: SEQ ID NO:4 including the restriction site for
     NdeI, the sequence encoding the polyhistidine tag, the restriction
     site for EcoRI, the sequence encoding the cleavage site for TEV,
     the restriction site for NdeI, and from the restriction site for
     XhoI

<400> SEQUENCE: 6 g aat tct gaa aac ttg tat ttc cag ggc agc cat atg atg ctg ctg gaa    49
  Asn Ser Glu Asn Leu Tyr Phe Gln Gly Ser His Met Met Leu Leu Glu
```

-continued

```
  1                 5                  10                 15
ggt ttt ctg gtt ggg ggc ggt gtt ccg ggt cca ggc acg gcc tgc ttg      97
Gly Phe Leu Val Gly Gly Gly Val Pro Gly Pro Gly Thr Ala Cys Leu
                20                  25                  30 acg aag gct ctg aaa gat agc ggt gac ctg ctg gtg gag tta gcg gtt     145
Thr Lys Ala Leu Lys Asp Ser Gly Asp Leu Leu Val Glu Leu Ala Val
            35                  40                  45 att att tgt gca tac cag aat ggc aaa gac ctt cag gag cag gac ttc     193
Ile Ile Cys Ala Tyr Gln Asn Gly Lys Asp Leu Gln Glu Gln Asp Phe
        50                  55                  60 aaa gaa ctg aag gaa ttg ctg gaa cgt aca ttg gaa cgt gcc ggt tgt     241
Lys Glu Leu Lys Glu Leu Leu Glu Arg Thr Leu Glu Arg Ala Gly Cys
65                  70                  75                  80 gcc ctc gat gat att gtg gcc gat tta ggt ctg gaa gaa ctg ctg ggc     289
Ala Leu Asp Asp Ile Val Ala Asp Leu Gly Leu Glu Glu Leu Leu Gly
                85                  90                  95 tcc atc ggc gtt agt acc ggc gat att atc cag ggt ctg tat aaa ctg     337
Ser Ile Gly Val Ser Thr Gly Asp Ile Ile Gln Gly Leu Tyr Lys Leu
                100                 105                 110 ttg aag gag tta aaa atc gac gag acc gtc ttt aat gcg gtc tgc gat     385
Leu Lys Glu Leu Lys Ile Asp Glu Thr Val Phe Asn Ala Val Cys Asp
            115                 120                 125 gtg acc aaa aaa atg ctg gat aac aag tgc tta ccg aaa att ctg caa     433
Val Thr Lys Lys Met Leu Asp Asn Lys Cys Leu Pro Lys Ile Leu Gln
        130                 135                 140 gga gat ctg gta aag ttc ctt gat ctg aag tat aaa gtt tgt att gaa     481
Gly Asp Leu Val Lys Phe Leu Asp Leu Lys Tyr Lys Val Cys Ile Glu
145                 150                 155                 160 ggt ggc gat cca gaa ctg att att aag gat ctg aaa atc atc ctg gaa     529
Gly Gly Asp Pro Glu Leu Ile Ile Lys Asp Leu Lys Ile Ile Leu Glu
                165                 170                 175 cgg ctt ccg tgt gtg ttg ggt gga gtc ggt ttg gat gat ctc ttt aag     577
Arg Leu Pro Cys Val Leu Gly Gly Val Gly Leu Asp Asp Leu Phe Lys
                180                 185                 190 aac att ttt gtt aag gat ggg att ctg tcc ttc gaa ggt att gcg aaa     625
Asn Ile Phe Val Lys Asp Gly Ile Leu Ser Phe Glu Gly Ile Ala Lys
            195                 200                 205 cct ctt ggt gac ctt ctc atc ctt gtc tta tgc ccg aac gtc aag aat     673
Pro Leu Gly Asp Leu Leu Ile Leu Val Leu Cys Pro Asn Val Lys Asn
        210                 215                 220 atc aat gta tcc tct taactcgag                                       697
Ile Asn Val Ser Ser
225
```

```
<210> SEQ ID NO 7
<211> LENGTH: 229
<212> TYPE: PRT
<213> ORGANISM: Artificial sequence
<220> FEATURE:
<223> OTHER INFORMATION: Synthetic Construct

<400> SEQUENCE: 7

Asn Ser Glu Asn Leu Tyr Phe Gln Gly Ser His Met Met Leu Leu Glu
1                 5                  10                  15

Gly Phe Leu Val Gly Gly Gly Val Pro Gly Pro Gly Thr Ala Cys Leu
                20                  25                  30

Thr Lys Ala Leu Lys Asp Ser Gly Asp Leu Leu Val Glu Leu Ala Val
            35                  40                  45

Ile Ile Cys Ala Tyr Gln Asn Gly Lys Asp Leu Gln Glu Gln Asp Phe
        50                  55                  60
```

```
Lys Glu Leu Lys Glu Leu Leu Glu Arg Thr Leu Glu Arg Ala Gly Cys
65                  70                  75                  80

Ala Leu Asp Asp Ile Val Ala Asp Leu Gly Leu Glu Glu Leu Leu Gly
                    85                  90                  95

Ser Ile Gly Val Ser Thr Gly Asp Ile Ile Gln Gly Leu Tyr Lys Leu
                100                 105                 110

Leu Lys Glu Leu Lys Ile Asp Glu Thr Val Phe Asn Ala Val Cys Asp
            115                 120                 125

Val Thr Lys Lys Met Leu Asp Asn Lys Cys Leu Pro Lys Ile Leu Gln
        130                 135                 140

Gly Asp Leu Val Lys Phe Leu Asp Leu Lys Tyr Lys Val Cys Ile Glu
145                 150                 155                 160

Gly Gly Asp Pro Glu Leu Ile Ile Lys Asp Leu Lys Ile Ile Leu Glu
                165                 170                 175

Arg Leu Pro Cys Val Leu Gly Gly Val Gly Leu Asp Asp Leu Phe Lys
            180                 185                 190

Asn Ile Phe Val Lys Asp Gly Ile Leu Ser Phe Glu Gly Ile Ala Lys
            195                 200                 205

Pro Leu Gly Asp Leu Leu Ile Leu Val Leu Cys Pro Asn Val Lys Asn
        210                 215                 220

Ile Asn Val Ser Ser
225

<210> SEQ ID NO 8
<211> LENGTH: 6395
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (1)..(6395)
<223> OTHER INFORMATION: pPBUFCBac-LvRsn1 expression vector resulting
      from the insertion of SEQ ID NO:6 into a vector for expression in
      bacteria
<220> FEATURE:
<221> NAME/KEY: CDS
<222> LOCATION: (112)..(819)

<400> SEQUENCE: 8
gatctcgatc ccgcgaaatt aatacgactc actataggggg aattgtgagc ggataacaat        60
tcccctctag aaataatttt gtttaaactt taagaaggag atatacatat g cat cat      117
                                                         His His
                                                          1 cat cat cat cac gtg aat tct gaa aac ttg tat ttc cag ggc agc cat     165
His His His His Val Asn Ser Glu Asn Leu Tyr Phe Gln Gly Ser His
            5                  10                  15 atg atg ctg ctg gaa ggt ttt ctg gtt ggg ggc ggt gtt ccg ggt cca     213
Met Met Leu Leu Glu Gly Phe Leu Val Gly Gly Gly Val Pro Gly Pro
        20                  25                  30 ggc acg gcc tgc ttg acg aag gct ctg aaa gat agc ggt gac ctg ctg     261
Gly Thr Ala Cys Leu Thr Lys Ala Leu Lys Asp Ser Gly Asp Leu Leu
35                  40                  45                  50 gtg gag tta gcg gtt att att tgt gca tac cag aat ggc aaa gac ctt     309
Val Glu Leu Ala Val Ile Ile Cys Ala Tyr Gln Asn Gly Lys Asp Leu
                55                  60                  65 cag gag cag gac ttc aaa gaa ctg aag gaa ttg ctg gaa cgt aca ttg     357
Gln Glu Gln Asp Phe Lys Glu Leu Lys Glu Leu Leu Glu Arg Thr Leu
            70                  75                  80
```

```
gaa cgt gcc ggt tgt gcc ctc gat gat att gtg gcc gat tta ggt ctg       405
Glu Arg Ala Gly Cys Ala Leu Asp Asp Ile Val Ala Asp Leu Gly Leu
        85                  90                  95 gaa gaa ctg ctg ggc tcc atc ggc gtt agt acc ggc gat att atc cag       453
Glu Glu Leu Leu Gly Ser Ile Gly Val Ser Thr Gly Asp Ile Ile Gln
    100                 105                 110 ggt ctg tat aaa ctg ttg aag gag tta aaa atc gac gag acc gtc ttt       501
Gly Leu Tyr Lys Leu Leu Lys Glu Leu Lys Ile Asp Glu Thr Val Phe
115                 120                 125                 130 aat gcg gtc tgc gat gtg acc aaa aaa atg ctg gat aac aag tgc tta       549
Asn Ala Val Cys Asp Val Thr Lys Lys Met Leu Asp Asn Lys Cys Leu
                135                 140                 145 ccg aaa att ctg caa gga gat ctg gta aag ttc ctt gat ctg aag tat       597
Pro Lys Ile Leu Gln Gly Asp Leu Val Lys Phe Leu Asp Leu Lys Tyr
            150                 155                 160 aaa gtt tgt att gaa ggt ggc gat cca gaa ctg att att aag gat ctg       645
Lys Val Cys Ile Glu Gly Gly Asp Pro Glu Leu Ile Ile Lys Asp Leu
            165                 170                 175 aaa atc atc ctg gaa cgg ctt ccg tgt gtg ttg ggt gga gtc ggt ttg       693
Lys Ile Ile Leu Glu Arg Leu Pro Cys Val Leu Gly Gly Val Gly Leu
        180                 185                 190 gat gat ctc ttt aag aac att ttt gtt aag gat ggg att ctg tcc ttc       741
Asp Asp Leu Phe Lys Asn Ile Phe Val Lys Asp Gly Ile Leu Ser Phe
195                 200                 205                 210 gaa ggt att gcg aaa cct ctt ggt gac ctt ctc atc ctt gtc tta tgc       789
Glu Gly Ile Ala Lys Pro Leu Gly Asp Leu Leu Ile Leu Val Leu Cys
                215                 220                 225 ccg aac gtc aag aat atc aat gta tcc tct taactcgaga tcgatgatat         839
Pro Asn Val Lys Asn Ile Asn Val Ser Ser
            230                 235 tcgagcctag gtataatcgg atccggctgc taacaaagcc cgaaaggaag ctgagttggc     899
tgctgccacc gctgagcaat aactagcata accccttggg gcctctaaac gggtcttgag     959
gggttttttg ctgaaaggag gaactatatc cggatatccc gcaagaggcc cggcagtacc     1019
ggcataacca agcctatgcc tacagcatcc agggtgacgg tgccgaggat gacgatgagc     1079
gcattgttag atttcataca cggtgcctga ctgcgttagc aatttaactg tgataaacta     1139
ccgcattaaa gctagcttat cgatgataag ctgtcaaaca tgagaattaa ttcttgaaga     1199
cgaaagggcc tcgtgatacg cctattttta taggttaatg tcatgataat aatggtttct     1259
tagacgtcag gtggcacttt tcggggaaat gtgcgcggaa cccctatttg tttatttttc     1319
taaatacatt caaatatgta tccgctcatg agacaataac cctgataaat gcttcaataa     1379
tattgaaaaa ggaagagtat gagtattcaa catttccgtg tcgcccttat tccctttttt     1439
gcggcatttt gccttcctgt ttttgctcac ccagaaacgc tggtgaaagt aaaagatgct     1499
gaagatcagt tgggtgcacg agtgggttac atcgaactgg atctcaacag cggtaagatc     1559
cttgagagtt ttcgccccga gaacgttttt ccaatgatga gcactttaa agttctgcta     1619 tgtggcgcgg tattatcccg tgttgacgcc gggcaagagc aactcggtcg ccgcatacac     1679
tattctcaga atgacttggt tgagtactca ccagtcacag aaaagcatct tacggatggc     1739
atgacagtaa gagaattatg cagtgctgcc ataaccatga gtgataacac tgcggccaac     1799
ttacttctga caacgatcgg aggaccgaag gagctaaccg cttttttgca caacatgggg     1859
gatcatgtaa ctcgccttga tcgttgggaa ccggagctga tgaagccat accaaacgac     1919 gagcgtgaca ccacgatgcc tgcagcaatg gcaacaacgt tgcgcaaact attaactggc     1979
gaactactta ctctagcttc ccggcaacaa ttaatagact ggatggaggc ggataaagtt     2039
```

```
gcaggaccac ttctgcgctc ggcccttccg gctggctggt ttattgctga taaatctgga    2099
gccggtgagc gtgggtctcg cggtatcatt gcagcactgg ggccagatgg taagccctcc    2159
cgtatcgtag ttatctacac dacggggagt caggcaacta tggatgaacg aaatagacag    2219
atcgctgaga taggtgcctc actgattaag cattggtaac tgtcagacca agtttactca    2279
tatatacttt agattgattt aaaacttcat ttttaattta aaaggatcta ggtgaagatc    2339 cttttttgata atctcatgac caaaatccct taacgtgagt tttcgttcca ctgagcgtca    2399
gaccccgtag aaaagatcaa aggatcttct tgagatcctt ttttttctgcg cgtaatctgc    2459 tgcttgcaaa caaaaaaacc accgctacca gcggtggttt gtttgccgga tcaagagcta    2519
ccaactcttt ttccgaaggt aactggcttc agcagagcgc agataccaaa tactgtcctt    2579
ctagtgtagc cgtagttagg ccaccacttc aagaactctg tagcaccgcc tacatacctc    2639
gctctgctaa tcctgttacc agtggctgct gccagtggcg ataagtcgtg tcttaccggg    2699
ttggactcaa gacgatagtt accggataag gcgcagcggt cgggctgaac ggggggttcg    2759
tgcacacagc ccagcttgga gcgaacgacc tacaccgaac tgagatacct acagcgtgag    2819
ctatgagaaa gcgccacgct tcccgaaggg agaaaggcgg acaggtatcc ggtaagcggc    2879
agggtcggaa caggagagcg cacgagggag cttccagggg gaaacgcctg gtatctttat    2939
agtcctgtcg ggtttcgcca cctctgactt gagcgtcgat ttttgtgatg ctcgtcaggg    2999
gggcggagcc tatggaaaaa cgccagcaac gcggcctttt tacggttcct ggccttttgc    3059
tggccttttg ctcacatgtt ctttcctgcg ttatcccctg attctgtgga taaccgtatt    3119
accgcctttg agtgagctga taccgctcgc cgcagccgaa cgaccgagcg cagcgagtca    3179
gtgagcgagg aagcggaaga gcgcctgatg cggtattttc tccttacgca tctgtgcggt    3239
atttcacacc gcaatggtgc actctcagta caatctgctc tgatgccgca tagttaagcc    3299
agtatacact ccgctatcgc tacgtgactg ggtcatggct gcgccccgac acccgccaac    3359
acccgctgac gcgccctgac gggcttgtct gctcccggca tccgcttaca gacaagctgt    3419
gaccgtctcc gggagctgca tgtgtcagag gttttcaccg tcatcaccga aacgcgcgag    3479
gcagctgcgg taaagctcat cagcgtggtc gtgaagcgat tcacagatgt ctgcctgttc    3539
atccgcgtcc agctcgttga gtttctccag aagcgttaat gtctggcttc tgataaagcg    3599
ggccatgtta agggcggttt tttcctgttt ggtcactgat gcctccgtgt aagggggatt    3659
tctgttcatg ggggtaatga taccgatgaa acgagagagg atgctcacga tacgggttac    3719
tgatgatgaa catgcccggt tactggaacg ttgtgagggg aaacaactgg cggtatggat    3779
gcggcgggac cagagaaaaa tcactcaggg tcaatgccag cgcttcgtta atacagatgt    3839
aggtgttcca cagggtagcc agcagcatcc tgcgatgcag atccggaaca taatggtgca    3899
gggcgctgac ttccgcgttt ccagacttta cgaaacacgg aaaccgaaga ccattcatgt    3959
tgttgctcag tcgcagacg ttttgcagca gcagtcgctt cacgttcgct cgcgtatcgg    4019
tgattcattc tgctaaccag taaggcaacc ccgccagcct agccgggtcc tcaacgacag    4079
gagcacgatc atgcgcaccc gtggccagga cccaacgctg cccgagatgc gccgcgtgcg    4139
gctgctggag atggcggacg cgatggatat gttctgccaa gggttggttt gcgcattcac    4199
agttctccgc aagaattgat tggctccaat tcttggagtg gtgaatccgt tagcgaggtg    4259
ccgccggctt ccattcaggt cgaggtggcc cggctccatg caccgcgacg caacgcgggg    4319
aggcagacaa ggtatagggc ggcgcctaca atccatgcca acccgttcca tgtgctcgcc    4379
```

-continued

```
gaggcggcat aaatcgccgt gacgatcagc ggtccaatga tcgaagttag gctggtaaga    4439
gccgcgagcg atccttgaag ctgtccctga tggtcgtcat ctacctgcct ggacagcatg    4499
gcctgcaacg cgggcatccc gatgccgccg gaagcgagaa gaatcataat ggggaaggcc    4559
atccagcctc gcgtcgcgaa cgccagcaag acgtagccca gcgcgtcggc cgccatgccg    4619
gcgataatgg cctgcttctc gccgaaacgt ttggtggcgg gaccagtgac gaaggcttga    4679
gcgagggcgt gcaagattcc gaataccgca agcgacaggc cgatcatcgt cgcgctccag    4739
cgaaagcggt cctcgccgaa aatgacccag agcgctgccg gcacctgtcc tacgagttgc    4799
atgataaaga agacagtcat aagtgcggcg acgatagtca tgccccgcgc ccaccggaag    4859
gagctgactg ggttgaaggc tctcaagggc atcggtcgag atcccggtgc ctaatgagtg    4919
agctaactta cattaattgc gttgcgctca ctgcccgctt tccagtcggg aaacctgtcg    4979
tgccagctgc attaatgaat cggccaacgc gcggggagag gcggtttgcg tattgggcgc    5039
cagggtggtt tttcttttca ccagtgagac gggcaacagc tgattgccct tcaccgcctg    5099
gccctgagag agttgcagca agcggtccac gctggtttgc cccagcaggc gaaaatcctg    5159
tttgatggtg gttaacggcg ggatataaca tgagctgtct tcggtatcgt cgtatcccac    5219
taccgagata tccgcaccaa cgcgcagccc ggactcggta atggcgcgca ttgcgcccag    5279
cgccatctga tcgttggcaa ccagcatcgc agtgggaacg atgccctcat tcagcatttg    5339
catggtttgt tgaaaccgga catggcactc cagtcgcctt cccgttccgc tatcggctga    5399
atttgattgc gagtgagata tttatgccag ccagccagac gcagacgcgc cgagacagaa    5459
cttaatgggc ccgctaacag cgcgatttgc tggtgaccca atgcgaccag atgctccacg    5519
cccagtcgcg taccgtcttc atgggagaaa ataatactgt tgatgggtgt ctggtcagag    5579
acatcaagaa ataacgccgg aacattagtg caggcagctt ccacagcaat ggcatcctgg    5639
tcatccagcg gatagttaat gatcagccca ctgacgcgtt gcgcgagaag attgtgcacc    5699
gccgctttac aggcttcgac gccgcttcgt tctaccatcg acaccaccac gctggcaccc    5759
agttgatcgg cgcgagattt aatcgccgcg acaatttgcg acggcgcgtg cagggccaga    5819
ctggaggtgg caacgccaat cagcaacgac tgtttgcccg ccagttgttg tgccacgcgg    5879
ttgggaatgt aattcagctc cgccatcgcc gcttccactt tttcccgcgt tttcgcagaa    5939
acgtggctgg cctggttcac cacgcgggaa acggtctgat aagagacacc ggcatactct    5999
gcgacatcgt ataacgttac tggtttcaca ttcaccaccc tgaattgact ctcttccggg    6059
cgctatcatg ccataccgcg aaaggttttg cgccattcga tggtgtccgg gatctcgacg    6119
ctctccctta tgcgactcct gcattaggaa gcagcccagt agtaggttga ggccgttgag    6179
caccgccgcc gcaaggaatg gtgcatgcaa ggagatggcg cccaacagtc ccccggccac    6239
ggggcctgcc accatacccca cgccgaaaca agcgctcatg agcccgaagt ggcgagcccg    6299
atcttcccca tcggtgatgt cggcgatata ggcgccagca accgcacctg tggcgccggt    6359
gatgccggcc acgatgcgtc cggcgtagag gatcga                               6395
```

<210> SEQ ID NO 9
<211> LENGTH: 236
<212> TYPE: PRT
<213> ORGANISM: Artificial sequence
<220> FEATURE:
<223> OTHER INFORMATION: Synthetic Construct

<400> SEQUENCE: 9

His His His His His His Val Asn Ser Glu Asn Leu Tyr Phe Gln Gly

-continued

```
1               5                    10                    15
Ser His Met Met Leu Leu Glu Gly Phe Leu Val Gly Gly Gly Val Pro
                20                    25                    30

Gly Pro Gly Thr Ala Cys Leu Thr Lys Ala Leu Lys Asp Ser Gly Asp
            35                    40                    45

Leu Leu Val Glu Leu Ala Val Ile Ile Cys Ala Tyr Gln Asn Gly Lys
        50                    55                    60

Asp Leu Gln Glu Gln Asp Phe Lys Glu Leu Lys Glu Leu Leu Glu Arg
65                    70                    75                    80

Thr Leu Glu Arg Ala Gly Cys Ala Leu Asp Asp Ile Val Ala Asp Leu
                85                    90                    95

Gly Leu Glu Glu Leu Leu Gly Ser Ile Gly Val Ser Thr Gly Asp Ile
            100                   105                   110

Ile Gln Gly Leu Tyr Lys Leu Leu Lys Glu Leu Lys Ile Asp Glu Thr
            115                   120                   125

Val Phe Asn Ala Val Cys Asp Val Thr Lys Lys Met Leu Asp Asn Lys
        130                   135                   140

Cys Leu Pro Lys Ile Leu Gln Gly Asp Leu Val Lys Phe Leu Asp Leu
145                   150                   155                   160

Lys Tyr Lys Val Cys Ile Glu Gly Gly Asp Pro Glu Leu Ile Ile Lys
                165                   170                   175

Asp Leu Lys Ile Ile Leu Glu Arg Leu Pro Cys Val Leu Gly Gly Val
            180                   185                   190

Gly Leu Asp Asp Leu Phe Lys Asn Ile Phe Val Lys Asp Gly Ile Leu
            195                   200                   205

Ser Phe Glu Gly Ile Ala Lys Pro Leu Gly Asp Leu Leu Ile Leu Val
        210                   215                   220

Leu Cys Pro Asn Val Lys Asn Ile Asn Val Ser Ser
225                   230                   235

<210> SEQ ID NO 10
<211> LENGTH: 236
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Amino acid sequence of the modified version of
      the surfactant protein LV-Rsn-1 encoded by the nucleotide sequence
      SEQ ID NO:6, which comprises SEQ ID NO:4

<400> SEQUENCE: 10

His His His His His His Val Asn Ser Glu Asn Leu Tyr Phe Gln Gly
1               5                    10                    15

Ser His Met Met Leu Leu Glu Gly Phe Leu Val Gly Gly Gly Val Pro
                20                    25                    30

Gly Pro Gly Thr Ala Cys Leu Thr Lys Ala Leu Lys Asp Ser Gly Asp
            35                    40                    45

Leu Leu Val Glu Leu Ala Val Ile Ile Cys Ala Tyr Gln Asn Gly Lys
        50                    55                    60

Asp Leu Gln Glu Gln Asp Phe Lys Glu Leu Lys Glu Leu Leu Glu Arg
65                    70                    75                    80

Thr Leu Glu Arg Ala Gly Cys Ala Leu Asp Asp Ile Val Ala Asp Leu
                85                    90                    95

Gly Leu Glu Glu Leu Leu Gly Ser Ile Gly Val Ser Thr Gly Asp Ile
            100                   105                   110
```

-continued

```
Ile Gln Gly Leu Tyr Lys Leu Leu Lys Glu Leu Lys Ile Asp Glu Thr
        115                 120                 125

Val Phe Asn Ala Val Cys Asp Val Thr Lys Lys Met Leu Asp Asn Lys
    130                 135                 140

Cys Leu Pro Lys Ile Leu Gln Gly Asp Leu Val Lys Phe Leu Asp Leu
145                 150                 155                 160

Lys Tyr Lys Val Cys Ile Glu Gly Gly Asp Pro Glu Leu Ile Ile Lys
                165                 170                 175

Asp Leu Lys Ile Ile Leu Glu Arg Leu Pro Cys Val Leu Gly Gly Val
                180                 185                 190

Gly Leu Asp Asp Leu Phe Lys Asn Ile Phe Val Lys Asp Gly Ile Leu
        195                 200                 205

Ser Phe Glu Gly Ile Ala Lys Pro Leu Gly Asp Leu Leu Ile Leu Val
    210                 215                 220

Leu Cys Pro Asn Val Lys Asn Ile Asn Val Ser Ser
225                 230                 235

<210> SEQ ID NO 11
<211> LENGTH: 648
<212> TYPE: DNA
<213> ORGANISM: Artificial sequence
<220> FEATURE:
<223> OTHER INFORMATION: Synthetic construct
<220> FEATURE:
<221> NAME/KEY: CDS
<222> LOCATION: (1)..(648)
<220> FEATURE:
<221> NAME/KEY: misc_feature
<222> LOCATION: (1)..(648)
<223> OTHER INFORMATION: Codon frequency optimization of SEQ ID NO:2 for
      yeast expression

<400> SEQUENCE: 11 ttg ttg gaa gga ttt ttg gtc gga ggt ggt gtc cct ggt cct ggt aca        48
Leu Leu Glu Gly Phe Leu Val Gly Gly Gly Val Pro Gly Pro Gly Thr
1               5                   10                  15 gca tgt ttg act aag gca ttg aaa gac agt gga gac ttg ttg gtt gag        96
Ala Cys Leu Thr Lys Ala Leu Lys Asp Ser Gly Asp Leu Leu Val Glu
            20                  25                  30 ttg gct gtt att att tgt gct tac caa aac ggt aaa gat ttg caa gag       144
Leu Ala Val Ile Ile Cys Ala Tyr Gln Asn Gly Lys Asp Leu Gln Glu
        35                  40                  45 caa gat ttc aag gaa ttg aag gag ttg ttg gaa aga act ttg gaa aga       192
Gln Asp Phe Lys Glu Leu Lys Glu Leu Leu Glu Arg Thr Leu Glu Arg
    50                  55                  60 gct ggt tgt gct ttg gat gat att gtt gct gat ttg ggt ttg gaa gag       240
Ala Gly Cys Ala Leu Asp Asp Ile Val Ala Asp Leu Gly Leu Glu Glu
65                  70                  75                  80 ttg ttg ggt tct att ggt gtt tct act gga gat atc atc caa ggt ttg       288
Leu Leu Gly Ser Ile Gly Val Ser Thr Gly Asp Ile Ile Gln Gly Leu
                85                  90                  95 tac aag ttg ttg aag gag ttg aag atc gat gaa act gtt ttt aac gct       336
Tyr Lys Leu Leu Lys Glu Leu Lys Ile Asp Glu Thr Val Phe Asn Ala
            100                 105                 110 gtt tgt gat gtt act aag aaa atg ttg gat aac aag tgt ttg cca aag       384
Val Cys Asp Val Thr Lys Lys Met Leu Asp Asn Lys Cys Leu Pro Lys
        115                 120                 125 atc ttg caa gga gat ttg gtt aag ttc ttg gat ttg aag tac aag gtt       432
Ile Leu Gln Gly Asp Leu Val Lys Phe Leu Asp Leu Lys Tyr Lys Val
    130                 135                 140
```

```
tgt atc gaa ggt gga gat cca gaa ttg att att aag gat ttg aag atc        480
Cys Ile Glu Gly Gly Asp Pro Glu Leu Ile Ile Lys Asp Leu Lys Ile
145             150             155             160 atc ttg gag aga ttg cct tgt gtt ttg ggt ggt gtt ggt ttg gat gat        528
Ile Leu Glu Arg Leu Pro Cys Val Leu Gly Gly Val Gly Leu Asp Asp
            165             170             175 ttg ttt aaa aac atc ttc gtt aag gat ggt att ttg tct ttc gaa ggt        576
Leu Phe Lys Asn Ile Phe Val Lys Asp Gly Ile Leu Ser Phe Glu Gly
            180             185             190 att gct aag cct ttg gga gat ttg ttg att ttg gtt ttg tgt cct aat        624
Ile Ala Lys Pro Leu Gly Asp Leu Leu Ile Leu Val Leu Cys Pro Asn
            195             200             205 gtc aag aat atc aat gtt tca tca                                        648
Val Lys Asn Ile Asn Val Ser Ser
    210             215
```

```
<210> SEQ ID NO 12
<211> LENGTH: 216
<212> TYPE: PRT
<213> ORGANISM: Artificial sequence
<220> FEATURE:
<223> OTHER INFORMATION: Synthetic Construct

<400> SEQUENCE: 12

Leu Leu Glu Gly Phe Leu Val Gly Gly Gly Val Pro Gly Pro Gly Thr
1               5               10              15

Ala Cys Leu Thr Lys Ala Leu Lys Asp Ser Gly Asp Leu Leu Val Glu
            20              25              30

Leu Ala Val Ile Ile Cys Ala Tyr Gln Asn Gly Lys Asp Leu Gln Glu
            35              40              45

Gln Asp Phe Lys Glu Leu Lys Glu Leu Leu Glu Arg Thr Leu Glu Arg
    50              55              60

Ala Gly Cys Ala Leu Asp Asp Ile Val Ala Asp Leu Gly Leu Glu Glu
65              70              75              80

Leu Leu Gly Ser Ile Gly Val Ser Thr Gly Asp Ile Ile Gln Gly Leu
            85              90              95

Tyr Lys Leu Leu Lys Glu Leu Lys Ile Asp Glu Thr Val Phe Asn Ala
            100             105             110

Val Cys Asp Val Thr Lys Lys Met Leu Asp Asn Lys Cys Leu Pro Lys
            115             120             125

Ile Leu Gln Gly Asp Leu Val Lys Phe Leu Asp Leu Lys Tyr Lys Val
            130             135             140

Cys Ile Glu Gly Gly Asp Pro Glu Leu Ile Ile Lys Asp Leu Lys Ile
145             150             155             160

Ile Leu Glu Arg Leu Pro Cys Val Leu Gly Gly Val Gly Leu Asp Asp
            165             170             175

Leu Phe Lys Asn Ile Phe Val Lys Asp Gly Ile Leu Ser Phe Glu Gly
            180             185             190

Ile Ala Lys Pro Leu Gly Asp Leu Leu Ile Leu Val Leu Cys Pro Asn
            195             200             205

Val Lys Asn Ile Asn Val Ser Ser
    210             215
```

```
<210> SEQ ID NO 13
<211> LENGTH: 685
<212> TYPE: DNA
<213> ORGANISM: Artificial sequence
<220> FEATURE:
<223> OTHER INFORMATION: Synthetic construct
```

-continued

```
<220> FEATURE:
<221> NAME/KEY: misc_feature
<222> LOCATION: (1)..(685)
<223> OTHER INFORMATION: SEQ ID NO:11 after addition of the restriction
      site for the PstI endonuclease, two nucleotides to place the
      coding sequence in the same frame of translation as the secretion
      factor alpha, and the restriction site for the endonuclease NotI
<220> FEATURE:
<221> NAME/KEY: CDS
<222> LOCATION: (3)..(683)

<400> SEQUENCE: 13 ct gca gga ttg ttg gaa gga ttt ttg gtc gga ggt ggt gtc cct ggt        47
   Ala Gly Leu Leu Glu Gly Phe Leu Val Gly Gly Gly Val Pro Gly
   1               5                   10                  15 cct ggt aca gca tgt ttg act aag gca ttg aaa gac agt gga gac ttg       95
Pro Gly Thr Ala Cys Leu Thr Lys Ala Leu Lys Asp Ser Gly Asp Leu
                20                  25                  30 ttg gtt gag ttg gct gtt att att tgt gct tac caa aac ggt aaa gat      143
Leu Val Glu Leu Ala Val Ile Ile Cys Ala Tyr Gln Asn Gly Lys Asp
            35                  40                  45 ttg caa gag caa gat ttc aag gaa ttg aag gag ttg ttg gaa aga act      191
Leu Gln Glu Gln Asp Phe Lys Glu Leu Lys Glu Leu Leu Glu Arg Thr
        50                  55                  60 ttg gaa aga gct ggt tgt gct ttg gat gat att gtt gct gat ttg ggt      239
Leu Glu Arg Ala Gly Cys Ala Leu Asp Asp Ile Val Ala Asp Leu Gly
    65                  70                  75 ttg gaa gag ttg ttg ggt tct att ggt gtt tct act gga gat atc atc      287
Leu Glu Glu Leu Leu Gly Ser Ile Gly Val Ser Thr Gly Asp Ile Ile
80                  85                  90                  95 caa ggt ttg tac aag ttg ttg aag gag ttg aag atc gat gaa act gtt      335
Gln Gly Leu Tyr Lys Leu Leu Lys Glu Leu Lys Ile Asp Glu Thr Val
                100                 105                 110 ttt aac gct gtt tgt gat gtt act aag aaa atg ttg gat aac aag tgt      383
Phe Asn Ala Val Cys Asp Val Thr Lys Lys Met Leu Asp Asn Lys Cys
            115                 120                 125 ttg cca aag atc ttg caa gga gat ttg gtt aag ttc ttg gat ttg aag      431
Leu Pro Lys Ile Leu Gln Gly Asp Leu Val Lys Phe Leu Asp Leu Lys
        130                 135                 140 tac aag gtt tgt atc gaa ggt gga gat cca gaa ttg att att aag gat      479
Tyr Lys Val Cys Ile Glu Gly Gly Asp Pro Glu Leu Ile Ile Lys Asp
    145                 150                 155 ttg aag atc atc ttg gag aga ttg cct tgt gtt ttg ggt ggt gtt ggt      527
Leu Lys Ile Ile Leu Glu Arg Leu Pro Cys Val Leu Gly Gly Val Gly
160                 165                 170                 175 ttg gat gat ttg ttt aaa aac atc ttc gtt aag gat ggt att ttg tct      575
Leu Asp Asp Leu Phe Lys Asn Ile Phe Val Lys Asp Gly Ile Leu Ser
                180                 185                 190 ttc gaa ggt att gct aag cct ttg gga gat ttg ttg att ttg gtt ttg      623
Phe Glu Gly Ile Ala Lys Pro Leu Gly Asp Leu Leu Ile Leu Val Leu
            195                 200                 205 tgt cct aat gtc aag aat atc aat gtt tca tca gag aac ctt tac ttt      671
Cys Pro Asn Val Lys Asn Ile Asn Val Ser Ser Glu Asn Leu Tyr Phe
        210                 215                 220 cag gga gcg gcc gc                                                    685
Gln Gly Ala Ala
    225

<210> SEQ ID NO 14
<211> LENGTH: 227
<212> TYPE: PRT
<213> ORGANISM: Artificial sequence
<220> FEATURE:
```

<223> OTHER INFORMATION: Synthetic Construct

<400> SEQUENCE: 14

```
Ala Gly Leu Leu Glu Gly Phe Leu Val Gly Gly Gly Val Pro Gly Pro
1               5                   10                  15

Gly Thr Ala Cys Leu Thr Lys Ala Leu Lys Asp Ser Gly Asp Leu Leu
            20                  25                  30

Val Glu Leu Ala Val Ile Ile Cys Ala Tyr Gln Asn Gly Lys Asp Leu
        35                  40                  45

Gln Glu Gln Asp Phe Lys Glu Leu Lys Glu Leu Leu Glu Arg Thr Leu
    50                  55                  60

Glu Arg Ala Gly Cys Ala Leu Asp Asp Ile Val Ala Asp Leu Gly Leu
65                  70                  75                  80

Glu Glu Leu Leu Gly Ser Ile Gly Val Ser Thr Gly Asp Ile Ile Gln
                85                  90                  95

Gly Leu Tyr Lys Leu Leu Lys Glu Leu Lys Ile Asp Glu Thr Val Phe
            100                 105                 110

Asn Ala Val Cys Asp Val Thr Lys Lys Met Leu Asp Asn Lys Cys Leu
        115                 120                 125

Pro Lys Ile Leu Gln Gly Asp Leu Val Lys Phe Leu Asp Leu Lys Tyr
    130                 135                 140

Lys Val Cys Ile Glu Gly Gly Asp Pro Glu Leu Ile Ile Lys Asp Leu
145                 150                 155                 160

Lys Ile Ile Leu Glu Arg Leu Pro Cys Val Leu Gly Gly Val Gly Leu
                165                 170                 175

Asp Asp Leu Phe Lys Asn Ile Phe Val Lys Asp Gly Ile Leu Ser Phe
            180                 185                 190

Glu Gly Ile Ala Lys Pro Leu Gly Asp Leu Leu Ile Leu Val Leu Cys
        195                 200                 205

Pro Asn Val Lys Asn Ile Asn Val Ser Ser Glu Asn Leu Tyr Phe Gln
    210                 215                 220

Gly Ala Ala
225
```

<210> SEQ ID NO 15
<211> LENGTH: 4219
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (1)..(4219)
<223> OTHER INFORMATION: pPBUFCYea-LvRsn1 expression vector resulting
     from insertion of SEQ ID NO:13 into a vector for expression in
     yeast
<220> FEATURE:
<221> NAME/KEY: CDS
<222> LOCATION: (941)..(1963)

<400> SEQUENCE: 15

```
agatctaaca tccaaagacg aaaggttgaa tgaaaccttt ttgccatccg acatccacag      60
gtccattctc acacataagt gccaaacgca acaggagggg atacactagc agcagaccgt     120
tgcaaacgca ggacctccac tcctcttctc ctcaacaccc acttttgcca tcgaaaaacc     180
agcccagtta ttgggcttga ttggagctcg ctcattccaa ttccttctat taggctacta     240
acaccatgac tttattagcc tgtctatcct ggcccccctg gcgaggttca tgtttgttta     300
tttccgaatg caacaagctc cgcattacac ccgaacatca ctccagatga gggctttctg     360
```

-continued

```
agtgtggggt caaatagttt catgttcccc aaatggccca aaactgacag tttaaacgct      420
gtcttggaac ctaatatgac aaaagcgtga tctcatccaa gatgaactaa gtttggttcg      480
ttgaaatgct aacggccagt tggtcaaaaa gaaacttcca aaagtcggca taccgtttgt      540
cttgtttggt attgattgac gaatgctcaa aaataatctc attaatgctt agcgcagtct      600
ctctatcgct tctgaacccc ggtgcacctg tgccgaaacg caaatgggga aacacccgct      660
ttttggatga ttatgcattg tctccacatt gtatgcttcc aagattctgg tgggaatact      720
gctgatagcc taacgttcat gatcaaaatt taactgttct aacccctact tgacagcaat      780
atataaacag aaggaagctg ccctgtctta aacctttttt tttatcatca ttattagctt      840
actttcataa ttgcgactgg ttccaattga caagcttttg attttaacga cttttaacga      900
caacttgaga agatcaaaaa acaactaatt attcgaaacg atg aga ttt cct tca      955
                                            Met Arg Phe Pro Ser
                                            1               5 att ttt act gct gtt tta ttc gca gca tcc tcc gca tta gct gct cca    1003
Ile Phe Thr Ala Val Leu Phe Ala Ala Ser Ser Ala Leu Ala Ala Pro
            10              15              20 gtc aac act aca aca gaa gat gaa acg gca caa att ccg gct gaa gct    1051
Val Asn Thr Thr Thr Glu Asp Glu Thr Ala Gln Ile Pro Ala Glu Ala
        25              30              35 gtc atc ggt tac tca gat tta gaa ggg gat ttc gat gtt gct gtt ttg    1099
Val Ile Gly Tyr Ser Asp Leu Glu Gly Asp Phe Asp Val Ala Val Leu
        40              45              50 cca ttt tcc aac agc aca aat aac ggg tta ttg ttt ata aat act act    1147
Pro Phe Ser Asn Ser Thr Asn Asn Gly Leu Leu Phe Ile Asn Thr Thr
    55              60              65 att gcc agc att gct gct aaa gaa gaa ggg gta tct ctc gag aaa aga    1195
Ile Ala Ser Ile Ala Ala Lys Glu Glu Gly Val Ser Leu Glu Lys Arg
70              75              80              85 gag gct gaa gct gca gga ttg ttg gaa gga ttt ttg gtc gga ggt ggt    1243
Glu Ala Glu Ala Ala Gly Leu Leu Glu Gly Phe Leu Val Gly Gly Gly
            90              95              100 gtc cct ggt cct ggt aca gca tgt ttg act aag gca ttg aaa gac agt    1291
Val Pro Gly Pro Gly Thr Ala Cys Leu Thr Lys Ala Leu Lys Asp Ser
        105             110             115 gga gac ttg ttg gtt gag ttg gct gtt att att tgt gct tac caa aac    1339
Gly Asp Leu Leu Val Glu Leu Ala Val Ile Ile Cys Ala Tyr Gln Asn
        120             125             130 ggt aaa gat ttg caa gag caa gat ttc aag gaa ttg aag gag ttg ttg    1387
Gly Lys Asp Leu Gln Glu Gln Asp Phe Lys Glu Leu Lys Glu Leu Leu
    135             140             145 gaa aga act ttg gaa aga gct ggt tgt gct ttg gat gat att gtt gct    1435
Glu Arg Thr Leu Glu Arg Ala Gly Cys Ala Leu Asp Asp Ile Val Ala
150             155             160             165 gat ttg ggt ttg gaa gag ttg ttg ggt tct att ggt gtt tct act gga    1483
Asp Leu Gly Leu Glu Glu Leu Leu Gly Ser Ile Gly Val Ser Thr Gly
            170             175             180 gat atc atc caa ggt ttg tac aag ttg ttg aag gag ttg aag atc gat    1531
Asp Ile Ile Gln Gly Leu Tyr Lys Leu Leu Lys Glu Leu Lys Ile Asp
            185             190             195 gaa act gtt ttt aac gct gtt tgt gat gtt act aag aaa atg ttg gat    1579
Glu Thr Val Phe Asn Ala Val Cys Asp Val Thr Lys Lys Met Leu Asp
            200             205             210 aac aag tgt ttg cca aag atc ttg caa gga gat ttg gtt aag ttc ttg    1627
Asn Lys Cys Leu Pro Lys Ile Leu Gln Gly Asp Leu Val Lys Phe Leu
            215             220             225
```

-continued

```
gat ttg aag tac aag gtt tgt atc gaa ggt gga gat cca gaa ttg att        1675
Asp Leu Lys Tyr Lys Val Cys Ile Glu Gly Gly Asp Pro Glu Leu Ile
230             235             240             245 att aag gat ttg aag atc atc ttg gag aga ttg cct tgt gtt ttg ggt        1723
Ile Lys Asp Leu Lys Ile Ile Leu Glu Arg Leu Pro Cys Val Leu Gly
                250             255             260 ggt gtt ggt ttg gat gat ttg ttt aaa aac atc ttc gtt aag gat ggt        1771
Gly Val Gly Leu Asp Asp Leu Phe Lys Asn Ile Phe Val Lys Asp Gly
            265             270             275 att ttg tct ttc gaa ggt att gct aag cct ttg gga gat ttg ttg att        1819
Ile Leu Ser Phe Glu Gly Ile Ala Lys Pro Leu Gly Asp Leu Leu Ile
        280             285             290 ttg gtt ttg tgt cct aat gtc aag aat atc aat gtt tca tca gag aac        1867
Leu Val Leu Cys Pro Asn Val Lys Asn Ile Asn Val Ser Ser Glu Asn
    295             300             305 ctt tac ttt cag gga gcg gcc gcc agc ttt cta gaa caa aaa ctc atc        1915
Leu Tyr Phe Gln Gly Ala Ala Ala Ser Phe Leu Glu Gln Lys Leu Ile
310             315             320             325 tca gaa gag gat ctg aat agc gcc gtc gac cat cat cat cat cat cat        1963
Ser Glu Glu Asp Leu Asn Ser Ala Val Asp His His His His His His
            330             335             340 tgagtttgta gccttagaca tgactgttcc tcagttcaag ttgggcactt acgagaagac        2023
cggtcttgct agattctaat caagaggatg tcagaatgcc atttgcctga gagatgcagg        2083
cttcattttt gatacttttt tatttgtaac ctatatagta taggattttt tttgtcattt        2143
tgtttcttct cgtacgagct tgctcctgat cagcctatct cgcagctgat gaatatcttg        2203
tggtaggggt ttgggaaaat cattcgagtt tgatgttttt cttggtattt cccactcctc        2263
ttcagagtac agaagattaa gtgagacctt cgtttgtgcg gatcccccac acaccatagc        2323
ttcaaaatgt ttctactcct tttttactct tccagatttt ctcggactcc gcgcatcgcc        2383
gtaccacttc aaaacaccca agcacagcat actaaatttt ccctctttct tcctctaggg        2443
tgtcgttaat tacccgtact aaaggtttgg aaaagaaaaa agagaccgcc tcgtttcttt        2503
ttcttcgtcg aaaaaggcaa taaaaatttt tatcacgttt ctttttcttg aaattttttt        2563
ttttagtttt tttctctttc agtgacctcc attgatattt aagttaataa acggtcttca        2623
atttctcaag tttcagtttc atttttcttg ttctattaca actttttta cttcttgttc        2683 attagaaaga aagcatagca atctaatcta aggggcggtg ttgacaatta atcatcggca        2743
tagtatatcg gcatagtata atacgacaag gtgaggaact aaaccatggc caagttgacc        2803
agtgccgttc cggtgctcac cgcgcgcgac gtcgccggag cggtcgagtt ctggaccgac        2863
cggctcgggt tctcccggga cttcgtggag gacgacttcg ccggtgtggt ccgggacgac        2923
gtgaccctgt tcatcagcgc ggtccaggac caggtggtgc cggacaacac cctggcctgg        2983
gtgtgggtgc gcggcctgga cgagctgtac gccgagtggt cggaggtcgt gtccacgaac        3043
ttccgggacg cctccgggcc ggccatgacc gagatcggcg agcagccgtg ggggcgggag        3103
ttcgccctgc gcgacccggc cggcaactgc gtgcacttcg tggccgagga caggactga         3163 cacgtccgac ggcggcccac gggtcccagg cctcggagat ccgtcccccct tttcctttgt       3223 cgatatcatg taattagtta tgtcacgctt acattcacgc cctcccccca catccgctct        3283
aaccgaaaag gaaggagtta gacaacctga agtctaggtc cctatttatt tttttatagt        3343
tatgttagta ttaagaacgt tatttatatt tcaaattttt cttttttttc tgtacagacg        3403
cgtgtacgca tgtaacatta tactgaaaac cttgcttgag aaggttttgg gacgctcgaa        3463
ggctttaatt tgcaagctgg agaccaacat gtgagcaaaa ggccagcaaa aggccaggaa        3523
```

-continued

```
ccgtaaaaag gccgcgttgc tggcgttttt ccataggctc cgcccccctg acgagcatca    3583
caaaaatcga cgctcaagtc agaggtggcg aaacccgaca ggactataaa gataccaggc    3643 gtttcccct ggaagctccc tcgtgcgctc tcctgttccg accctgccgc ttaccggata    3703
cctgtccgcc tttctccctt cgggaagcgt ggcgctttct caatgctcac gctgtaggta    3763
tctcagttcg gtgtaggtcg ttcgctccaa gctgggctgt gtgcacgaac cccccgttca    3823
gcccgaccgc tgcgccttat ccggtaacta tcgtcttgag tccaacccgg taagacacga    3883
cttatcgcca ctggcagcag ccactggtaa caggattagc agagcgaggt atgtaggcgg    3943
tgctacagag ttcttgaagt ggtggcctaa ctacggctac actagaagga cagtatttgg    4003
tatctgcgct ctgctgaagc cagttacctt cggaaaaaga gttggtagct cttgatccgg    4063
caaacaaacc accgctggta gcggtggttt ttttgtttgc aagcagcaga ttacgcgcag    4123
aaaaaaagga tctcaagaag atcctttgat cttttctacg gggtctgacg ctcagtggaa    4183
cgaaaactca cgttaaggga ttttggtcat gagatc    4219
```

```
<210> SEQ ID NO 16
<211> LENGTH: 341
<212> TYPE: PRT
<213> ORGANISM: Artificial sequence
<220> FEATURE:
<223> OTHER INFORMATION: Synthetic Construct

<400> SEQUENCE: 16

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Ala Gly Leu Leu Glu Gly Phe
                85                  90                  95

Leu Val Gly Gly Gly Val Pro Gly Pro Gly Thr Ala Cys Leu Thr Lys
            100                 105                 110

Ala Leu Lys Asp Ser Gly Asp Leu Leu Val Glu Leu Ala Val Ile Ile
            115                 120                 125

Cys Ala Tyr Gln Asn Gly Lys Asp Leu Gln Glu Gln Asp Phe Lys Glu
        130                 135                 140

Leu Lys Glu Leu Leu Glu Arg Thr Leu Glu Arg Ala Gly Cys Ala Leu
145                 150                 155                 160

Asp Asp Ile Val Ala Asp Leu Gly Leu Glu Glu Leu Leu Gly Ser Ile
                165                 170                 175

Gly Val Ser Thr Gly Asp Ile Ile Gln Gly Leu Tyr Lys Leu Leu Lys
            180                 185                 190

Glu Leu Lys Ile Asp Glu Thr Val Phe Asn Ala Val Cys Asp Val Thr
            195                 200                 205

Lys Lys Met Leu Asp Asn Lys Cys Leu Pro Lys Ile Leu Gln Gly Asp
        210                 215                 220

Leu Val Lys Phe Leu Asp Leu Lys Tyr Lys Val Cys Ile Glu Gly Gly
225                 230                 235                 240
```

-continued

```
Asp Pro Glu Leu Ile Ile Lys Asp Leu Lys Ile Ile Leu Glu Arg Leu
            245             250             255

Pro Cys Val Leu Gly Gly Val Gly Leu Asp Asp Leu Phe Lys Asn Ile
            260             265             270

Phe Val Lys Asp Gly Ile Leu Ser Phe Glu Gly Ile Ala Lys Pro Leu
            275             280             285

Gly Asp Leu Leu Ile Leu Val Leu Cys Pro Asn Val Lys Asn Ile Asn
        290             295             300

Val Ser Ser Glu Asn Leu Tyr Phe Gln Gly Ala Ala Ala Ser Phe Leu
305             310             315             320

Glu Gln Lys Leu Ile Ser Glu Glu Asp Leu Asn Ser Ala Val Asp His
            325             330             335

His His His His His
            340
```

<210> SEQ ID NO 17
<211> LENGTH: 341
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Amino acid sequence of the modified version of
      the surfactant protein Lv-Rsn-1 encoded by the nucleotide sequence
      SEQ ID NO:11, which in turn is contained in SEQ ID NO:13

<400> SEQUENCE: 17

```
Met Arg Phe Pro Ser Ile Phe Thr Ala Val Leu Phe Ala Ala Ser Ser
1               5               10              15

Ala Leu Ala Ala Pro Val Asn Thr Thr Thr Glu Asp Glu Thr Ala Gln
            20              25              30

Ile Pro Ala Glu Ala Val Ile Gly Tyr Ser Asp Leu Glu Gly Asp Phe
        35              40              45

Asp Val Ala Val Leu Pro Phe Ser Asn Ser Thr Asn Asn Gly Leu Leu
        50              55              60

Phe Ile Asn Thr Thr Ile Ala Ser Ile Ala Ala Lys Glu Glu Gly Val
65              70              75              80

Ser Leu Glu Lys Arg Glu Ala Glu Ala Ala Gly Leu Leu Glu Gly Phe
            85              90              95

Leu Val Gly Gly Gly Val Pro Gly Pro Gly Thr Ala Cys Leu Thr Lys
            100             105             110

Ala Leu Lys Asp Ser Gly Asp Leu Leu Val Glu Leu Ala Val Ile Ile
            115             120             125

Cys Ala Tyr Gln Asn Gly Lys Asp Leu Gln Glu Gln Asp Phe Lys Glu
        130             135             140

Leu Lys Glu Leu Leu Glu Arg Thr Leu Glu Arg Ala Gly Cys Ala Leu
145             150             155             160

Asp Asp Ile Val Ala Asp Leu Gly Leu Glu Glu Leu Leu Gly Ser Ile
            165             170             175

Gly Val Ser Thr Gly Asp Ile Ile Gln Gly Leu Tyr Lys Leu Leu Lys
            180             185             190

Glu Leu Lys Ile Asp Glu Thr Val Phe Asn Ala Val Cys Asp Val Thr
        195             200             205

Lys Lys Met Leu Asp Asn Lys Cys Leu Pro Lys Ile Leu Gln Gly Asp
        210             215             220
```

```
Leu Val Lys Phe Leu Asp Leu Lys Tyr Lys Val Cys Ile Glu Gly Gly
225             230             235             240

Asp Pro Glu Leu Ile Ile Lys Asp Leu Lys Ile Ile Leu Glu Arg Leu
                245             250             255

Pro Cys Val Leu Gly Gly Val Gly Leu Asp Asp Leu Phe Lys Asn Ile
                260             265             270

Phe Val Lys Asp Gly Ile Leu Ser Phe Glu Gly Ile Ala Lys Pro Leu
            275             280             285

Gly Asp Leu Leu Ile Leu Val Leu Cys Pro Asn Val Lys Asn Ile Asn
        290             295             300

Val Ser Ser Glu Asn Leu Tyr Phe Gln Gly Ala Ala Ala Ser Phe Leu
305             310             315             320

Glu Gln Lys Leu Ile Ser Glu Glu Asp Leu Asn Ser Ala Val Asp His
                325             330             335

His His His His His
                340
```